US012680992B2

(12) United States Patent
Seike et al.

(10) Patent No.: US 12,680,992 B2
(45) Date of Patent: Jul. 14, 2026

(54) GAS SENSOR

(71) Applicant: NGK INSULATORS, LTD., Nagoya (JP)

(72) Inventors: Yuya Seike, Nagoya (JP); Shintaro Maki, Nagoya (JP); Kohei Yaita, Nagoya (JP); Kota Katagiri, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 282 days.

(21) Appl. No.: 18/499,573

(22) Filed: Nov. 1, 2023

(65) Prior Publication Data

US 2024/0241097 A1 Jul. 18, 2024

(30) Foreign Application Priority Data

Jan. 18, 2023 (JP) ................................. 2023-006196

(51) Int. Cl.
G01N 33/00 (2006.01)
G01M 15/10 (2006.01)

(52) U.S. Cl.
CPC ....... G01N 33/0009 (2013.01); G01M 15/102 (2013.01)

(58) Field of Classification Search
CPC ........... G01N 33/0009; G01N 27/4078; G01N 33/0037; G01M 15/102
See application file for complete search history.

(56) References Cited

U.S. PATENT DOCUMENTS

| | | | | |
|---|---|---|---|---|
| 2004/0045822 A1* | 3/2004 | Kojima | .............. | G01N 27/4077 |
| | | | | 204/408 |
| 2009/0223818 A1* | 9/2009 | Matsui | .............. | G01N 27/4062 |
| | | | | 204/412 |
| 2012/0255356 A1 | 10/2012 | Kume et al. | | |
| 2014/0290333 A1* | 10/2014 | Hirata | ................ | G01N 27/4078 |
| | | | | 73/23.2 |

(Continued)

FOREIGN PATENT DOCUMENTS

| | | |
|---|---|---|
| DE | 10 2012 205 618 A1 | 10/2012 |
| DE | 10 2014 208 049 A1 | 10/2014 |

(Continued)

OTHER PUBLICATIONS

German Office Acrion received in corresponding German Office Action received in corresponding German Application No. 10 2023 135 737.9 dated May 11, 2026.

*Primary Examiner* — Thomas M Hammond, III
(74) *Attorney, Agent, or Firm* — MATTINGLY & MALUR, PC

(57) ABSTRACT

Provided is a gas sensor that is low in risk of erosion of an elastic body even when the gas sensor is shortened and prevents a lead retaining portion from coming into contact with an inner surface of a through-hole of the elastic body or closing the through-hole. In the gas sensor according to one aspect of the present invention, one diameter-reduced portion for fixing the elastic body to a tubular body is provided, the lead retaining portion is apart from a front end surface of the elastic body by 0.1 mm or more, and a size or the like of each member is adjusted to satisfy a predetermined relational expression, thereby preventing the occurrence of contact misalignment.

9 Claims, 3 Drawing Sheets

(56)                           References Cited

U.S. PATENT DOCUMENTS

2014/0318228  A1     10/2014  Nomura et al.
2021/0018461  A1      1/2021  Liu et al.
2021/0063342  A1*     3/2021  Watanabe  .......... G01N 27/4078

FOREIGN PATENT DOCUMENTS

DE       10 2020 208 595  A1    10/2021
JP            2014-196917  A    10/2014

* cited by examiner

FRONT END   REAR END

REAR END ↔ FRONT END

FRONT END ◄——► REAR END

GAS SENSOR

CROSS-REFERENCE TO RELATED APPLICATION

The present application claims priority from Japanese application JP 2023-006196, filed on Jan. 18, 2023, the contents of which is hereby incorporated by reference into this application.

FIELD OF INVENTION

The present invention relates to a gas sensor.

BACKGROUND

Conventionally, a gas sensor used for measuring the concentration of a specific gas component such as oxygen or $NO_x$ in a gas being measured such as an exhaust gas of an automobile is known. Such a gas sensor includes, for example, a tubular body accommodating a sensor element, a lead extending outward from an open end of the tubular body, a metal terminal electrically connecting the sensor element and the lead, and an elastic body that is disposed to seal the open end and into which the lead is inserted. For the gas sensor having such a configuration, various attempts are known for preventing a connection section between the metal terminal and the sensor element from suffering misalignment (contact misalignment) while improving the accuracy of gas concentration detection by maintaining sealing performance of the elastic body high enough. For example, JP 2014-196917A described below discloses the following gas sensor. That is, in the gas sensor disclosed in JP 2014-196917A, the open end of the tubular body is sealed by the elastic body having a through-hole provided therein, and a lead retaining portion of the terminal fitting that crimps and retain the lead and the lead are accommodated in the through-hole. Then, in the gas sensor disclosed in JP 2014-196917A, a rear end of the tubular body is swaged in two places spaced apart from each other at a predetermined interval in an axial direction, and the elastic body is swaged by the two diameter-reduced portions in multi-stages (specifically, two stages) and fixed to the tubular body.

SUMMARY OF INVENTION

The inventors of the present invention have found that the gas sensor (conventional gas sensor) having the configuration disclosed in JP 2014-196917A has the following problem.

First, in the conventional gas sensor, in order to fix the elastic body to the tubular body, the tubular body is swaged in two places spaced apart from each other at the predetermined interval in the axial direction. That is, the elastic body of the conventional gas sensor extends, inside the tubular body, from the open end of the tubular body to at least a swaging position adjacent to a front end of the tubular body of the two swaging positions. It is therefore required that, for the conventional gas sensor in which the two diameter-reduced portions are provided in the tubular body to fix the elastic body to the tubular body, the length of the elastic body increase in the axial direction as compared with a case where only one diameter-reduced portion is provided. Then, in the conventional gas sensor, when the length of the entire gas sensor in the axial direction is reduced, that is, when the gas sensor is shortened, the following problem occurs. That is, when the length of the entire gas sensor in the axial direction is reduced with the length of the elastic body in the axial direction maintained, it is difficult to make a distance between a front end of the gas sensor, particularly, a heat source located at the front end of the gas sensor and the elastic body long enough. Therefore, in the conventional gas sensor, in a case where the length of the entire gas sensor in the axial direction is to be reduced, the distance between the heat source and the elastic body cannot be made long enough, and there is a possibility that the elastic body is exposed to a high temperature to suffer erosion. That is, the inventors of the present invention have found a problem that, in a case where the conventional gas sensor is shortened, the risk of erosion of the elastic body increases.

Second, in the conventional gas sensor, the lead retaining portion of the terminal fitting that crimps and retains the lead is accommodated in the through-hole provided inside the elastic body. Then, in the conventional gas sensor, a periphery of the elastic body is swaged by the two diameter-reduced portions, so that an inner surface of the through-hole and the lead retaining portion are in contact with each other. Therefore, in the conventional gas sensor, the inner surface of the through-hole and the lead retaining portion come in contact with each other due to, for example, vibrations of the gas sensor caused by use in a severe environment, long-term use, or the like, and there is a risk of deteriorating airtightness in the tubular body. That is, the inventors of the present invention have found a problem that there is a risk for the conventional gas sensor that the lead retaining portion comes into contact with the inner surface of the through-hole of the elastic body to reduce the sealing performance of the elastic body and deteriorate the airtightness in the tubular body.

Third, in the conventional gas sensor, the periphery of the elastic body is swaged by the two diameter-reduced portions, so that there is a possibility that the lead retaining portion accommodated in the through-hole completely closes (in other words, completely blocks) the through-hole. Here, in the gas sensor, for example, when outside air and gas in the tubular body flow through a space between a covering and a metal wire (conductor) of the lead (in other words, the inside of the covering), the outside air is introduced into the tubular body, and the gas in the tubular body is released to the outside. However, when the lead retaining portion completely blocks the through-hole, there is a risk that gas is prevented from being replaced and circulated between the inside of the tubular body and the external space, thereby deteriorating the sensor measurement accuracy of the gas sensor. That is, the inventors of the present invention have found a problem that there is a risk for the conventional gas sensor that the lead retaining portion closes the through-hole of the elastic body to deteriorate the sensor measurement accuracy.

The present invention, in one aspect, has been made in view of such circumstances, and it is therefore an object of the present invention to provide a gas sensor that is low in risk of erosion of an elastic body even when the gas sensor is shortened, and prevents a lead retaining portion from coming into contact with an inner surface of a through-hole of the elastic body or closing the through-hole.

In order to solve the above-described problems, the present invention has the following configuration.

A gas sensor according to a first aspect includes a sensor element extending in an axial direction, the sensor element including a detection portion at a front end and an element electrode at a rear end, a terminal fitting extending in the axial direction and having a front end electrically connected to the element electrode, a tubular body in which the sensor element and the terminal fitting are arranged, a lead electrically connected to a rear end of the terminal fitting and extending outward from an open end at a rear end of the tubular body, and an elastic body disposed to seal the open end, the elastic body having a through-hole extending in the axial direction provided therein, the through-hole accommodating a covered section of the lead, in which a lead retaining portion that crimps and retains the lead is provided at the rear end of the terminal fitting, one diameter-reduced portion that swages a part of the elastic body from a periphery of the elastic body is provided in the tubular body, the lead retaining portion is apart from an end surface of a front end of the elastic body by 0.1 mm or more in the axial direction, and an expression (1) given below is satisfied:

$$(Da - Db) \times Sa > Fc/(\mu \times q). \qquad \text{expression (1)}$$

In the expression (1), "Da" denotes a diameter of an unswaged section that is a section of the elastic body not swaged by the diameter-reduced portion, "Db" denotes a diameter of a swaged section that is a section of the elastic body swaged by the diameter-reduced portion, "Sa" denotes a surface area of a section of the covered section of the lead accommodated in the through-hole in the swaged section, "Fc" denotes a magnitude of a load in the axial direction that interrupts electrical connection between the element electrode and the terminal fitting, "$\mu$" denotes a coefficient of static friction between the elastic body and the covered section of the lead, and "q" denotes pressure per unit area applied to the covered section of the lead by the elastic body when the diameter-reduced portion radially swages the elastic body by a unit length.

With this configuration, in the gas sensor, the number of the diameter-reduced portions provided in the tubular body to fix the elastic body to the tubular body is "one". Therefore, the gas sensor can reduce the length of the elastic body in the axial direction as compared with the conventional gas sensor in which "two" diameter-reduced portions for fixing the elastic body to the tubular body are provided in the tubular body at a predetermined interval.

Therefore, even in a case where the length of the entire gas sensor in the axial direction is reduced (shortened), the gas sensor can make the distance between the elastic body that seals the open end at the rear end of the tubular body and the front end of the gas sensor long enough. That is, even in a case where the gas sensor is shortened as a whole, the gas sensor can make the distance between the elastic body and the heat source located at the front end of the gas sensor long enough. Therefore, even in a case where the gas sensor is shortened as a whole, the gas sensor can produce an effect of preventing, by making the distance between the elastic body and the heat source long enough, the occurrence of a situation in which the elastic body is exposed to a high temperature to suffer erosion.

Further, in the gas sensor, the lead retaining portion is not in the through-hole of the elastic body, and specifically, the lead retaining portion is apart from the end surface of the front end of the elastic body by 0.1 mm or more in the axial direction.

Therefore, in the gas sensor, the lead retaining portion neither comes into contact with the inner surface of the through-hole of the elastic body nor blocks the through-hole. That is, the gas sensor can produce an effect of preventing the lead retaining portion from coming into contact with the inner surface of the through-hole of the elastic body and preventing the lead retaining portion from blocking the through-hole of the elastic body.

Here, in a case where the number of the diameter-reduced portions for fixing the elastic body to the tubular body is "one", it may be difficult for the elastic body (particularly, the swaged section) to restrict the movement of the lead in the axial direction. That is, in a case where the number of the diameter-reduced portions is one, the lead may easily move in the axial direction. Then, as the lead easily moves in the axial direction, the terminal fitting crimped to the lead in the lead retaining portion also easily moves in the axial direction, so that the electrical connection between the terminal fitting and the element electrode of the sensor element is easily lost (easily interrupted). Therefore, in a case where the number of the diameter-reduced portions is one, contact misalignment (interruption of the electrical connection between the terminal fitting and the element electrode of the sensor element) may easily occur in the gas sensor.

Therefore, adjusting the size or the like of each member to satisfy the expression (1) allows the gas sensor to prevent the occurrence of contact misalignment. That is, the gas sensor including each member whose size or the like has been adjusted to satisfy the expression (1) allows the elastic body (particularly, the swaged section provided only in one place corresponding to the diameter-reduced portion provided only in one place) to restrict the movement of the lead in the axial direction to prevent the occurrence of contact misalignment. Specifically, in the gas sensor, the diameter Da of the unswaged section, the diameter Db of the swaged section, the surface area Sa, the coefficient of static friction $\mu$, and the pressure q produced when swaged by the unit length satisfy the expression (1).

The inventors of the present invention have verified that the elastic body (particularly, the swaged section) restricts the movement of the lead in the axial direction as follows. That is, swaging the elastic body accommodating the covered section of the lead in the through-hole provided inside the elastic body from the periphery of the elastic body causes a radial force (vertical drag Fn) to act on the lead (particularly, the covered section). As a result, a static frictional force Ff proportional to the coefficient of static friction $\mu$ between the elastic body and the covered section and the vertical drag Fn is generated against the movement of the lead in the axial direction. That is, "Ff=$\mu \times$Fn" holds. The static frictional force Ff restricts the movement of the lead in the axial direction.

The vertical drag Fn is proportional to the pressure q produced when swaged by the unit length, a difference between the diameter Da of the unswaged section and the diameter Db of the swaged section, and the surface area Sa. That is, "Fn=(Da−Db)$\times$Sa$\times$q" holds. As described above, the pressure q produced when swaged by the unit length indicates pressure per unit area applied to the covered section by the elastic body when the elastic body is radially swaged by the unit length. Further, the surface area Sa is the surface area of the part of the covered section accommodated in the swaged section (more precisely, the through-hole in the swaged section). Note that, in a case where the covered section of each of a plurality of the leads is accommodated in a corresponding one of a plurality of the through-holes provided inside the elastic body, the surface area Sa is expressed as follows. That is, it is expressed as "Sa=Do$\times$La$\times$Nm" using an outer diameter (circumferential length) Do of each of the plurality of leads, a length La, in the axial direction, of the swaged section, and the number Nm of the plurality of leads.

As described above, since "Ff=μ×Fn" and "Fn=(Da−Db)× Sa×q" hold, the static frictional force Ff between the elastic body and the covered section is expressed as $$\text{``}Ff = \mu \times (Da - Db) \times Sa \times q\text{''}.$$

Then, the inventors of the present invention have verified the magnitude of the load in the axial direction that causes contact misalignment by conducting a test of pulling the lead in the axial direction on the gas sensor in which the terminal fitting and the element electrode are electrically connected to each other. As a result, the inventors of the present invention have verified that (the magnitude of) the load in the axial direction that causes contact misalignment is equal to (the magnitude of) the load Fc in the axial direction. That is, the inventors of the present invention have verified that the magnitude of the force (load) to pull the lead in the axial direction when contact misalignment occurs (that is, the electrical connection between the terminal fitting and the element electrode is interrupted) is equal to the magnitude of the load Fc in the axial direction.

It is therefore possible to prevent the occurrence of contact misalignment by making (the magnitude of) the static frictional force Ff larger than (the magnitude of) the load Fc in the axial direction. As described above, since "Ff=μ×(Da−Db)×Sa×q" holds, it is possible to prevent the occurrence of contact misalignment by satisfying "μ×(Da−Db)×Sa×q>Fc". The relational expression is transformed into "(Da−Db)×Sa>Fc/(μ×q)" given as the expression (1).

Therefore, the gas sensor in which the diameter Da of the unswaged section, the diameter Db of the swaged section, the surface area Sa of the covered section, the coefficient of static friction μ, and the pressure q produced when swaged by the unit length satisfy the expression (1) can prevent the occurrence of contact misalignment.

Furthermore, since the number of the diameter-reduced portions provided in the tubular body is one, the gas sensor can reduce the number of items whose dimensions are to be managed and reduce the number of man-hours required for inspection and the inspection cost as compared with the conventional gas sensor in which two diameter-reduced portions are provided in the tubular body at a predetermined interval. As described above, since the elastic body of the gas sensor can be shortened as compared with the conventional gas sensor, the material cost of the elastic body can be reduced, and the number of choices of the material of the elastic body can be further increased to allow the selection of the most suitable material.

A gas sensor according to a second aspect that is based on the gas sensor according to the first aspect may further includes a ceramic housing accommodating the element electrode and a front end section of the terminal fitting electrically connected to the element electrode, and a spacer disposed between the ceramic housing and the elastic body in the axial direction.

With this configuration, the gas sensor further includes the ceramic housing and the spacer. That is, in the gas sensor, the elastic body is disposed adjacent to the rear end in the axial direction relative to the ceramic housing and the spacer. Therefore, the gas sensor can produce an effect of reducing transfer of heat generated from the heat source located at the front end of the gas sensor to the elastic body more effectively by means of the ceramic housing and the spacer. Note that the spacer disposed adjacent to the front end relative to the elastic body in the axial direction preferably includes a heat-resistant material. When the spacer includes a heat-resistant material, it is possible to prevent the occurrence of a situation in which the spacer disposed adjacent to the front end relative to the elastic body in the axial direction is eroded by heat generated from the heat source.

In a gas sensor according to a third aspect that is based on the gas sensor according to the second aspect, the lead retaining portion of the terminal fitting may be disposed inside the spacer. With this configuration, in the gas sensor, the lead retaining portion of the terminal fitting is disposed inside the spacer. Therefore, the gas sensor can produce an effect of preventing the lead retaining portion from coming into contact with the elastic body or closing the through-hole of the elastic body more effectively.

In a gas sensor according to a fourth aspect that is based on the gas sensor according to any one of the first to third aspects, the material of the elastic body may be fluoro-rubber. With this configuration, in the gas sensor, the material of the elastic body is fluoro-rubber with excellent properties in various aspects such as resistance and strength, and particularly with excellent heat resistance and oil resistance. Therefore, the gas sensor can produce an effect of maintaining the sealing performance of the elastic body high enough to maintain or improve the accuracy of gas concentration detection even in, for example, a high-temperature environment.

In a gas sensor according to a fifth aspect that is based on the gas sensor according to any one of the first to fourth aspects, the covered section of the lead may be covered with fluoro-resin. With this configuration, in the gas sensor, the covering material of the lead is fluoro-resin that is low in dielectric constant and is excellent in insulation durability, heat resistance, and the like. Therefore, the gas sensor can produce an effect of increasing efficiency, miniaturization and precision, and the like.

In a gas sensor according to a sixth aspect that is based on the gas sensor according to any one of the first to fifth aspects, the diameter Da of the unswaged section and the diameter Db of the swaged section may satisfy an expression (2) given below:

$$Db/Da \geq 0.5. \qquad\qquad \text{expression (2)}$$

With this configuration, in the gas sensor, the diameter Da of the unswaged section and the diameter Db of the swaged section of the elastic body satisfy the expression (2), that is, the diameter Db of the swaged section is greater than or equal to 50% of the diameter Da of the unswaged section. The inventors of the present invention have verified that the following problem occurs when the diameter Db of the swaged section is less than 50% of the diameter Da of the unswaged section. That is, it has been verified that a gap is generated between the tubular body and the elastic body, which causes a problem such as deterioration in the sealing performance of the elastic body (the airtightness in the tubular body achieved by the elastic body). Therefore, when the diameter Db of the swaged section is set greater than or equal to 50% of the diameter Da of the unswaged section, the gas sensor can produce an effect of maintaining the sealing performance of the elastic body high enough to maintain or improve the accuracy of gas concentration detection.

According to the present invention, it is possible to provide the gas sensor that is low in risk of erosion of the elastic body even when the gas sensor is shortened and prevents the lead retaining portion from coming into contact with the inner surface of the through-hole of the elastic body or closing the through-hole.

DETAILED DESCRIPTION OF THE PREFERRED EMBODIMENTS

Figure 1:
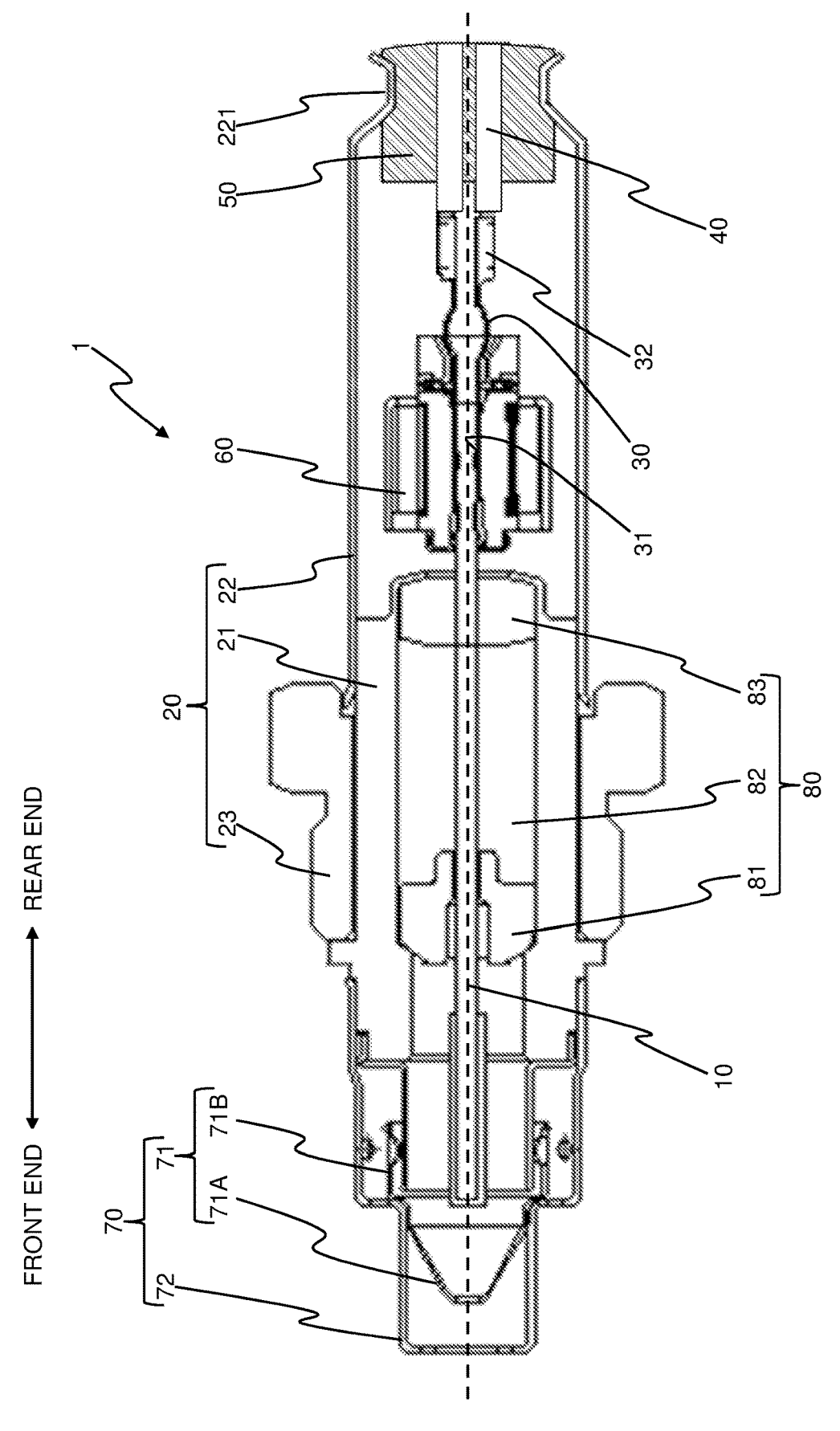
FIG. 1 is a schematic cross-sectional view schematically illustrating an example of a configuration of a gas sensor according to an embodiment.

Hereinafter, an embodiment (hereinafter, also referred to as "present embodiment") according to one aspect of the present invention will be described with reference to the drawings. The present embodiment described below, however, is merely an example of the present invention in all respects. It goes without saying that various improvements or modifications can be made without departing from the scope of the present invention. That is, in carrying out the present invention, a specific configuration according to the embodiment may be employed as appropriate.

The inventors of the present invention have found that a conventional gas sensor in which an elastic body having a lead retaining portion of a terminal fitting and a lead accommodated in a through-hole provided therein is swaged by two diameter-reduced portions of a tubular body spaced apart from each other at a predetermined interval in an axial direction has the following problem. That is, the inventors of the present invention have found a problem that when the gas sensor is shortened as a whole, the risk of erosion of the elastic body increases, and there is also a risk that the lead retaining portion comes into contact with the inner surface of the through-hole of the elastic body or closes the through-hole, thereby deteriorating airtightness in the tubular body and sensor measurement accuracy.

Therefore, in a gas sensor according to one aspect of the present invention, a tubular body having an open end at its rear end sealed by an elastic body has only one diameter-reduced portion provided therein by which a part of the elastic body is swaged from the periphery of the elastic body. That is, the gas sensor according to one aspect of the present invention includes one diameter-reduced portion. Further, in the gas sensor according to one aspect of the present invention, a distance between an end surface of a front end of the elastic body and a lead retaining portion of a terminal fitting in the axial direction is greater than or equal to 0.1 mm. That is, in the gas sensor according to one aspect of the present invention, the lead retaining portion is not accommodated in the through-hole of the elastic body, and specifically, the lead retaining portion is disposed at a position 0.1 mm or more apart from the elastic body (the end surface of the front end of the elastic body).

The gas sensor according to one aspect of the present invention includes one diameter-reduced portion for fixing the elastic body to the tubular body, so that a length of the elastic body in the axial direction can be reduced as compared with the conventional gas sensor having two diameter-reduced portions provided at a predetermined interval in the axial direction. Accordingly, it is possible for the gas sensor according to one aspect of the present invention to make, even when the gas sensor is shortened as a whole, a distance between the elastic body that seals the open end at the rear end of the tubular body and a heat source located at the front end of the gas sensor long enough. It is therefore possible for the gas sensor according to one aspect of the present invention to prevent, by making the distance between the elastic body and the heat source long enough even in a case where the gas sensor is shortened as a whole, the occurrence of a situation in which the elastic body is exposed to a high temperature to suffer erosion.

Further, in the gas sensor according to one aspect of the present invention, the lead retaining portion of the terminal fitting is separated from the elastic body (the front end surface of the elastic body) by 0.1 mm or more in the axial direction, thereby preventing the occurrence of a situation in which the lead retaining portion comes into contact with the inner surface of the through-hole of the elastic body or closes the through-hole. Accordingly, it is possible for the gas sensor according to one aspect of the present invention to reduce a risk that the lead retaining portion comes into contact with the inner surface of the through-hole of the elastic body or closes the through-hole, thereby deteriorating airtightness in the tubular body and sensor measurement accuracy.

Furthermore, in the gas sensor according to one aspect of the present invention, the size or the like of each member is adjusted to satisfy a predetermined condition (relational expression), so as to prevent the lead from moving in the axial direction to cause contact misalignment even in a case where the number of diameter-reduced portions is one. Specifically, in the gas sensor according to one aspect of the present invention, the size or the like of each member is adjusted to satisfy an expression (1) to be described later. The inventors of the present invention have verified that adjusting the size or the like of each member to satisfy the expression (1) can restrict the movement of the lead in the axial direction to prevent the occurrence of contact misalignment even in a case where the number of diameter-reduced portions is one. It is therefore possible for the gas sensor according to one aspect of the present invention having each member adjusted in size or the like to satisfy the expression (1) to prevent the occurrence of contact misalignment even in a case where the number of diameter-reduced portions is one.

As described above, the gas sensor according to one aspect of the present invention includes one diameter-reduced portion for fixing the elastic body to the tubular body, and the lead retaining portion of the terminal fitting is disposed at a position 0.1 mm or more apart from the elastic body (the end surface of the front end of the elastic body) in the axial direction. Then, in the gas sensor according to one aspect of the present invention, the size or the like of each member is adjusted to satisfy the expression (1). With such a configuration, the gas sensor according to one aspect of the present invention is low in risk of erosion of the elastic body even when the gas sensor is shortened, and can prevent the lead retaining portion from coming into contact with the inner surface of the through-hole of the elastic body or closing the through-hole and further prevent the occurrence of contact misalignment. Hereinafter, first, a gas sensor 1 will be described as the gas sensor according to one aspect of the present invention with reference to FIGS. 1 and 2.

Configuration Example

<Overview of Entire Gas Sensor>

FIG. 1 is a schematic cross-sectional view schematically illustrating an example of a configuration of the gas sensor 1 according to the present embodiment. That is, FIG. 1 schematically illustrates a cross-sectional configuration of the gas sensor 1 parallel to and in contact with a longitudinal axis (axis line, line along the left-right direction of drawing). The gas sensor 1 is an example of the "gas sensor" of the present invention, and is a gas sensor capable of detecting a concentration of a specific gas (specific gas concentration) such as oxygen or $NO_x$ in a gas being measured such as an exhaust gas of an automobile. As illustrated in FIG. 1, the gas sensor 1 has an axis extending along the longitudinal direction (axial direction), and has a front end and a rear end as both ends in the longitudinal direction. One end in the longitudinal direction is the front end, and the other end is the rear end. In the example in FIG. 1, the gas sensor 1 is disposed such that the front end of the gas sensor 1 faces left, and the rear end of the gas sensor 1 faces right. That is, the left-right direction of FIG. 1 corresponds to the longitudinal direction (axial direction). In the present embodiment, the gas sensor 1 includes a sensor element 10, a tubular body 20, a terminal fitting 30, a lead 40, an elastic body 50, a ceramic housing 60, and a protective cover 70. In the gas sensor 1, the sensor element 10 is enclosed by the tubular body 20 and the protective cover 70, and the tubular body 20 and the protective cover 70 constitute, as a whole, a housing member (casing) that accommodates the sensor element 10. The sensor element 10 is disposed coaxially with the tubular body 20 and the protective cover 70, and the extending direction of the central axis of the sensor element 10 coincides with the axial direction of the gas sensor 1.

(Sensor Element)

The sensor element 10 is an example of the "sensor element" of the present invention, and extends along the axial direction (left-right direction of FIG. 1). The sensor element 10 illustrated in FIG. 1 is an elongated flat plate-shaped (elongated plate-shaped) element. The sensor element 10 includes a detection portion (not illustrated) at the front end and an element electrode (not illustrated) at the rear end. The front end of the sensor element 10 illustrated in FIG. 1 is covered with an outer porous layer, and the outer porous layer serves as a protective layer that prevents the occurrence of a crack in the element body of the sensor element 10 due to adhesion of moisture or the like in the gas being measured, for example.

In the gas sensor 1, the sensor element 10 is disposed such that the front end faces toward the front end of the gas sensor 1. For example, in one aspect of the sensor element 10, the gas being measured that has been introduced into the sensor element 10 is reduced or decomposed inside the sensor element 10 to produce oxygen ions. In the gas sensor 1 including such a sensor element 10, the concentration of the specific gas that is a gas to be detected in the gas being measured is obtained on the basis of the fact that the amount of oxygen ions flowing through the sensor element 10 is proportional to the concentration of the specific gas.

In the example illustrated in FIG. 1, the front end of the sensor element 10 is enclosed by the protective cover 70, the rear end protrudes into an outer tube 22, and an approximately central section between the front end and the rear end is fixed inside a main fitting 21 by an annular-fitting component 80 having both ends airtightly sealed.

(Annular-Fitting Component)

In the example illustrated in FIG. 1, the annular-fitting component 80 includes a first ceramic supporter 81, a green compact 82, and a second ceramic supporter 83. The first ceramic supporter 81 and the second ceramic supporter 83 are ceramic insulators. More specifically, the first ceramic supporter 81 and the second ceramic supporter 83 each have a through-hole (not illustrated) provided, at its axis center position, in a shape corresponding to the cross-sectional shape of the sensor element 10, and the sensor element 10 is inserted into the through-hole to fit the first ceramic supporter 81 and the second ceramic supporter 83 around the sensor element 10. Note that the first ceramic supporter 81 is retained by a tapered surface of the main fitting 21 on the left side of the drawing.

On the other hand, the green compact 82 is obtained by molding ceramic powder such as talc. The green compact 82 is obtained by compressing, into a single piece, two molded bodies (not illustrated) that are fitted around the sensor element 10 by the insertion of the sensor element 10 into the through-hole, as with the first ceramic supporter 81 and the second ceramic supporter 83, and arranged inside the main fitting 21 with the two molded bodies fitted around sensor element 10. More specifically, ceramic particles constituting the green compact 82 are enclosed by the first ceramic supporter 81, the second ceramic supporter 83, and the main fitting 21, and densely fills a space in the main fitting 21 through which the sensor element 10 extends. The compression filling of the green compact 82 allows the front end and the rear end of the sensor element 10 to be airtightly sealed.

FIG. 1 illustrates an example in which the annular-fitting component 80 includes the first ceramic supporter 81, the green compact 82, and the second ceramic supporter 83. The annular-fitting component 80 of the gas sensor 1, however, need not necessarily include the first ceramic supporter 81, the green compact 82, and the second ceramic supporter 83. The gas sensor 1 illustrated in FIG. 1 includes the annular-fitting component 80 that fixes the sensor element 10 inside the main fitting 21 and airtightly seals the front end and the rear end of the sensor element 10.

(Tubular Body)

The tubular body 20 is an example of the "tubular body" of the present invention. The tubular body 20 is, for example, a tubular (for example, a cylindrical) member made of metal, and has an open end. The sensor element 10 and the terminal fitting 30 are arranged inside the tubular body 20. In the example illustrated in FIG. 1, the tubular body 20 includes the main fitting 21 having a tubular shape, the outer tube 22 having a tubular shape, and a fixing bolt 23, each of which is a metal member.

The main fitting 21 is a tubular (for example, a cylindrical) member made of metal. In the main fitting 21, the sensor element 10 and the annular-fitting component 80 for fixing fitted around the sensor element 10 are accommodated. That is, the main fitting 21 is further fitted around the annular-fitting component 80 fitted around the sensor element 10. The main fitting 21 illustrated in FIG. 1 surrounds the sensor element 10 along the axial direction (longitudinal direction), and in particular, surrounds the sensor element 10 excluding a part of each of the front end and the rear end of the sensor element 10.

The outer tube 22 is a tubular (for example, a cylindrical) member made of metal, and the outer tube 22 illustrated in FIG. 1 covers the periphery of the rear end of the sensor element 10 and the periphery of the ceramic housing 60 (terminal fitting 30).

The outer tube 22 has a front end (open end) welded and fixed to an outer periphery of the rear end of the main fitting 21. Further, the elastic body 50 is disposed in an open end at a rear end of the outer tube 22 so as to seal the open end. Provided at the rear end of the outer tube 22 is a diameter-reduced portion 221 that swages a part of the elastic body 50 for sealing the open end at the rear end from the periphery of the elastic body 50. The diameter-reduced portion 221 is an example of the "diameter-reduced portion" of the present invention. The outer tube 22 is swaged by the diameter-reduced portion 221 from the outside into a diameter-reduced shape over the entire circumferential direction of the outer tube 22, so that a reaction force directed radially outward is generated in the elastic body 50 to seal the outer tube 22.

Further, the lead 40 is drawn out from the open end at the rear end of the outer tube 22 sealed by the elastic body 50 through the through-hole (not illustrated) provided inside the elastic body 50. Outside air (air) is introduced into the internal space of the outer tube 22 through a space between a covering and a metal wire (conductor) of the lead 40 (in other words, the inside of the covering), and the internal space of the outer tube 22 becomes a reference gas (air) atmosphere accordingly. The rear end of the sensor element 10 is disposed in the internal space of the outer tube 22 filled with the reference gas.

The fixing bolt 23 is an annular member used to fix the gas sensor 1 to a measurement position (attachment position), and is fixed coaxially with the main fitting 21. The fixing bolt 23 includes a threaded bolt portion and a retaining portion retained when the bolt portion is screwed. The bolt portion of the fixing bolt 23 is screwed into a nut provided at the attachment position of the gas sensor 1. For example, when the bolt portion of the fixing bolt 23 is screwed into a nut (nut portion) provided in an exhaust pipe of an automobile, the gas sensor 1 is fixed to the exhaust pipe with a side of the gas sensor 1 adjacent to the protective cover 70 exposed to the exhaust pipe.

As described above, the tubular body 20 illustrated in FIG. 1 includes the main fitting 21, the outer tube 22, and the fixing bolt 23, and is configured as a tubular (for example, a cylindrical) member as a whole, particularly as a tubular member extending in the axial direction. That is, the tubular body 20 illustrated in FIG. 1 is a cylindrical member, extending in the axial direction, including the main fitting 21 having a tubular shape, the outer tube 22 having a tubular shape and welded and fixed to the outer periphery of the rear end of the main fitting 21, and the fixing bolt 23 disposed at the outer periphery of the front end of the main fitting 21. For example, the tubular body 20 and the gas sensor 1 (sensor element 10) are coaxial, and the tubular body 20 has the front end and the rear end as both ends in the axial direction (longitudinal direction) and is disposed such that the front end of the tubular body 20 faces toward the front end of the gas sensor 1. The tubular body 20 accommodates the sensor element 10, the annular-fitting component 80 for fixing fitted around the sensor element 10, and the ceramic housing 60 (terminal fitting 30), and has the open end at the rear end sealed by the elastic body 50. The diameter-reduced portion 221 for fixing the elastic body 50 for sealing the open end of the tubular body 20 is provided at the rear end of the tubular body 20 (outer tube 22), and the diameter-reduced portion 221 swages a part of the elastic body 50 from the periphery of the elastic body 50.

Note that the tubular body 20 of the gas sensor 1 need not necessarily include the main fitting 21, the outer tube 22, and the fixing bolt 23. The tubular body 20 need not include the fixing bolt 23, or the main fitting 21 and the outer tube 22 may be integrated into a single member. In the gas sensor 1, the tubular body 20 only needs to be a tubular member in which the sensor element 10 is disposed and that has an open end.

(Terminal Fitting)

The terminal fitting 30 is an example of the "terminal fitting" of the present invention. The terminal fitting 30 is a metal member (contact member) extending in the axial direction. In the gas sensor 1, the sensor element 10 (particularly, the element electrode) and the lead 40 are electrically connected to each other via the terminal fitting 30. As illustrated in FIG. 1, the terminal fitting 30 includes, at the front end, an element contact portion 31 electrically connected to the element electrode of the sensor element 10, and includes, at the rear end, a lead retaining portion 32 that crimps and retains the lead 40.

For example, the element contact portion 31 located at the front end of the terminal fitting 30 is in contact with the element electrode of the sensor element 10 with the element contact portion 31 hooked to the ceramic housing 60, and the lead retaining portion 32 located at the rear end of the terminal fitting 30 crimps and retains the lead 40. In the terminal fitting 30, a section between the element contact portion 31 and the lead retaining portion 32 may have a leaf spring shape. In the example illustrated in FIG. 1, the lead retaining portion 32 of the terminal fitting 30 is disposed adjacent to the front end relative to the elastic body 50 in the axial direction. Further, the element contact portion 31 of the terminal fitting 30 is accommodated in the ceramic housing 60, that is, the element contact portion 31 and the element electrode of the sensor element 10 are electrically connected to each other in the ceramic housing 60.

(Ceramic Housing)

The ceramic housing 60 is an example of the "ceramic housing" of the present invention. The ceramic housing 60 is a ceramic member that accommodates the rear end of the sensor element 10 (specifically, the element electrode provided at the rear end of the sensor element 10) and the front end (specifically, the element contact portion 31) of the terminal fitting 30. That is, in the gas sensor 1 illustrated in FIG. 1, the sensor element 10 (particularly, the element electrode) and the terminal fitting 30 (particularly, the element contact portion 31) are electrically connected to each other in the ceramic housing 60.

For example, the rear end of the sensor element 10 provided with the element electrode is inserted into the ceramic housing 60 accommodating the front end (element contact portion 31) of the terminal fitting 30. In this insertion state, the element electrode provided at the rear end of the sensor element 10 and the front end (element contact portion 31) of the terminal fitting 30 are in contact with each other. The front end (element contact portion 31) of the terminal fitting 30 may be interposed and fixed between the rear end of the sensor element 10 provided with the element electrode and the ceramic housing 60 to electrically connect the element electrode of the sensor element 10 and the terminal fitting 30.

A position (for example, a position in the axial direction) of the ceramic housing 60 in the tubular body 20 is fixed, and, in particular, the movement toward the front end is restricted. The position of the ceramic housing 60 in the axial direction in the tubular body 20 is fixed by, for example, a ceramic housing fixing member (not illustrated), and, in particular, the movement toward the front end is restricted. The ceramic housing fixing member may include, for example, a spring member that presses the ceramic housing 60 radially inward in the tubular body 20, and a swaging ring that exerts a spring force by pressing the spring member.

(Lead)

The lead 40 is an example of the "lead" of the present invention. The lead 40 is electrically connected to the element electrode of the sensor element 10 via the terminal fitting 30, and extends outward from the open end of the tubular body 20. Specifically, the lead 40 has its front end electrically connected to the rear end (that is, the lead retaining portion 32) of the terminal fitting 30, and has its rear end extending outward from the open end of the tubular body 20. Then, as described above, the gap between the lead 40 and the tubular body 20 (outer tube 22) is sealed by the elastic body 50.

For example, the lead 40 is inserted into the through-hole (not illustrated) provided inside the elastic body 50. The front end of the lead 40 (specifically, an uncovered section 42 to be described with reference to FIG. 2) is crimped and fixed to the rear end of the terminal fitting 30 (lead retaining portion 32), and the rear end of the lead 40 is connected to an external device (controller), a power supply, or the like. As a result, the sensor element 10 (particularly, the element electrode of the sensor element 10) is electrically connected to the external device, the power supply, or the like via the terminal fitting 30 and the lead 40. Note that FIG. 1 illustrates an example where there are two terminal fittings 30 and two leads 40, but this is merely given for the sake of simplicity of illustration. In practice, the gas sensor 1 includes the terminal fittings 30 and the leads 40 as many as necessary for the above-described electrical connection.

In the gas sensor 1, for example, when outside air and gas in the tubular body 20 flow through a space between the covering and the metal wire (conductor) of the lead 40 (in other words, the inside of the covering), outside air is introduced into the tubular body 20, and gas in the tubular body 20 is released to the outside.

(Elastic Body)

The elastic body 50 is an example of the "elastic body" of the present invention. The elastic body 50 is a member having elasticity, and is made of, for example, rubber. The elastic body 50 is disposed to seal the open end (in the example illustrated in FIG. 1, the open end at the rear end) of the tubular body 20, and the lead 40 is inserted into the elastic body 50. Specifically, the through-hole extending in the axial direction is provided inside the elastic body 50, and for example, a plurality of through-holes extending in the axial direction are provided. The lead 40 (particularly, a covered section 41) is accommodated (inserted) in the through-hole provided inside the elastic body 50, and for example, each of a plurality of the leads 40 is accommodated (inserted) in a corresponding one of the plurality of through-holes provided inside the elastic body 50.

The material of the elastic body 50 is, for example, fluoro-rubber. fluoro-rubber has excellent properties in various aspects such as resistance and strength, and is particularly excellent in heat resistance and oil resistance. Therefore, when the elastic body 50 made of fluoro-rubber is used, the gas sensor 1 can produce an effect of maintaining the sealing performance of the elastic body 50 high enough to maintain or improve the accuracy of gas concentration detection even in, for example, a high-temperature environment. For the gas sensor 1, the elastic body 50, however, need not necessarily be made of fluoro-rubber, and the elastic body 50 may be made of any desired material having elasticity.

(Protective Cover)

The protective cover 70 is an exterior member having an approximately cylindrical shape that protects a predetermined area of the front end of the sensor element 10, which is a section that directly comes into contact with the gas being measured during use. The protective cover 70 illustrated in FIG. 1 surrounds at least a part of the front end of the tubular body 20 (main fitting 21) along the axial direction (longitudinal direction) and extends beyond the front end of the sensor element 10. For example, the protective cover 70 surrounds a part of the front end of the sensor element 10 and a part of the front end of the tubular body 20 around the axis. The protective cover 70 has a front end and a rear end as both ends in the axial direction, and the front end of the protective cover 70 is disposed adjacent to the front end of the gas sensor 1 relative to the front end of the sensor element 10.

The protective cover 70 is provided with a plurality of through-holes (not illustrated) through which gas can flow. The gas being measured flowing into the protective cover 70 through the through-holes becomes a gas to be directly detected by the sensor element 10. Note that the type, number, arrangement position, shape, and the like of the through-holes provided in the protective cover 70 may be determined as appropriate in consideration of the inflow mode of the gas being measured into the protective cover 70.

In the example illustrated in FIG. 1, the protective cover 70 includes a bottomed tubular inner cover 71 that covers the front end of the sensor element 10 and a bottomed tubular outer cover 72 that covers the inner cover 71. The inner cover 71 includes a first member 71B and a second member 71A, and covers the periphery of at least a part of the front end of the sensor element 10 and the periphery of at least a part of the front end of the tubular body 20 (main fitting 21). The first member 71B extends along the axial direction from an outer wall of the front end of the tubular body 20, and further extends along the axial direction after its diameter decreases in a direction orthogonal to the axial direction just beyond the front end of the tubular body 20. The second member 71A covers the periphery of a part of the front end of the first member 71B. The outer cover 72 covers the periphery of the inner cover 71.

A sensor element chamber is provided as a space surrounded by the inner cover 71, and the front end of the sensor element 10 is disposed in the sensor element chamber. An opening is provided as appropriate in the first member 71B and the second member 71A of the inner cover 71, and the outer cover 72 so as to allow the sensor element chamber to communicate with a space outside the protective cover 70. The configuration and shape of the protective cover 70, however, are not limited to such an example. The configuration and shape of the protective cover 70 may be determined as appropriate in accordance with the embodiment.

As the material of the protective cover 70, a metal material such as stainless steel (for example, SUS) may be used. The metal material may be appropriately formed into the protective cover 70. Note that the protective cover 70 may be omitted from the configuration of the gas sensor 1.

<Details of Rear End of Gas Sensor>

Figure 2:
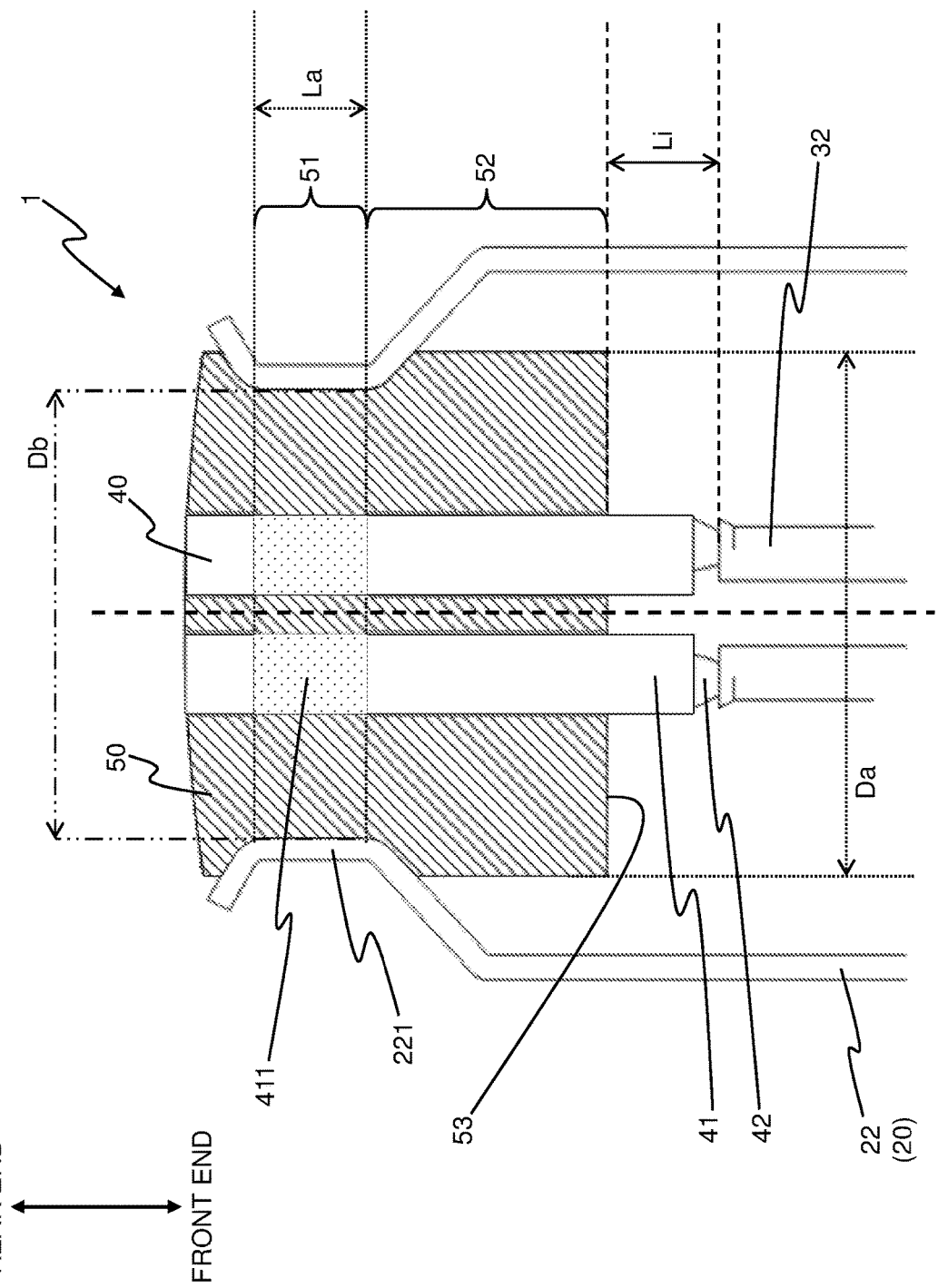
FIG. 2 is a schematic cross-sectional view illustrating an example of a main configuration of the gas sensor in FIG. 1.

FIG. 2 is an enlarged cross-sectional view schematically illustrating a main part of the gas sensor 1. Specifically, FIG. 2 illustrates details of the rear end of the gas sensor 1. In FIG. 2, the vertical direction of the paper corresponds to the axial direction (longitudinal direction) of the gas sensor 1 (sensor element 10), the lower side of the paper corresponds to the front end, and the upper side of the paper corresponds to the rear end.

(Regarding Number of Diameter-Reduced Portions and the Like)

As illustrated in FIG. 2, in the gas sensor 1, "one" diameter-reduced portion 221 that "swages a part of the elastic body 50 from the periphery of the elastic body 50" is provided in the tubular body 20 (outer tube 22), and for example, the "one" diameter-reduced portion is provided at the rear end of the tubular body 20. The elastic body 50 includes a swaged section 51 that is a section swaged by the "one" diameter-reduced portion 221 and an unswaged section 52 that is a section adjacent to the front end relative to the swaged section 51 in the axial direction. The unswaged section 52 can also be regarded as a section that is located adjacent to the front end relative to the swaged section 51 in the axial direction and is not swaged by the diameter-reduced portion 221. A front end surface 53 of the elastic body 50 is an end surface of the front end of the elastic body 50 in the axial direction, and can also be regarded as a front end surface of the swaged section 51.

In the example illustrated in FIG. 2, "Da" denotes a diameter (unit: [mm]) of the unswaged section 52 that is a section of the elastic body 50 not swaged by the diameter-reduced portion 221. In the example illustrated in FIG. 2, the diameter Da of the unswaged section 52 can also be regarded as the diameter of the front end surface 53 of the elastic body 50. Further, "Db" denotes a diameter (unit: [mm]) of the swaged section 51 that is a section of the elastic body 50 swaged by the diameter-reduced portion 221. In the gas sensor 1, the diameter Db of the swaged section 51 is greater than or equal to 50% of the diameter Da of the unswaged section 52.

Further, in the following description, pressure per unit area applied to the covered section 41 of the lead 40 by the elastic body 50 when the elastic body 50 is radially swaged by the unit length by the diameter-reduced portion 221 is referred to as "pressure q produced when swaged by the unit length" (unit: [N/mm$^3$]). In the following description, the "pressure q produced when swaged by the unit length" may be simply abbreviated as "pressure q". The pressure q can also be regarded as "pressure per unit area applied to a pressed section 411 of the lead 40 by the elastic body 50 when the elastic body 50 is radially swaged by the unit length by the diameter-reduced portion 221". Details of the pressed section 411 of the lead 40 will be described later.

The lead 40 is inserted into the elastic body 50, and in particular, as illustrated in FIG. 2, the covered section 41 of the lead 40 is accommodated inside the elastic body 50. Specifically, as described above, the through-hole extending in the axial direction is provided inside the elastic body 50, and the lead 40, particularly the covered section 41 of the lead 40, is accommodated in the through-hole.

The lead 40 includes the covered section 41 that is a section covered with a predetermined covering material and the uncovered section 42 that is a section not covered with the covering material. The uncovered section 42 can also be regarded as a bare metal wire (conductor) that is not covered with the covering material, and is crimped to the lead retaining portion 32 of the terminal fitting 30.

The covered section 41 of the lead 40 is covered with, for example, fluoro-resin, that is, the covering material of the lead 40 is, for example, fluoro-resin. The fluoro-resin is low in dielectric constant and is excellent in insulation durability, heat resistance, and the like. Therefore, when fluoro-resin is used as the covering material of the lead 40, the gas sensor 1 can produce an effect of increasing efficiency, miniaturization and precision, and the like, for example. For the gas sensor 1, the covering material of the lead 40, however, need not necessarily be fluoro-resin, and the gas sensor 1 may use, as the covering material of the lead, a material suitable as the covering material of the lead 40 as appropriate.

Of the covered section 41 of the lead 40, a section accommodated in the through-hole in the swaged section 51 of the elastic body 50 is the pressed section 411. The pressed section 411 can also be regarded as a "section that is accommodated in the through-hole provided inside the swaged section 51 and has its outer peripheral surface pressed by the inner surface of the through-hole" in the covered section 41 of the lead 40.

Further, in the following description, a surface area of the pressed section 411 of the lead 40 is referred to as "surface area Sa" (unit: [mm$^2$]). That is, the "surface area Sa" is the surface area of the pressed section 411 that is the "section of the covered section 41 of the lead 40 accommodated in the through-hole in the swaged section 51 of the elastic body 50". For example, in a case where the gas sensor 1 includes the "elastic body 50 in which a plurality of through-holes extending in the axial direction are provided" and each of the plurality of leads 40 is accommodated in a corresponding one of the plurality of through-holes, the surface area Sa of the pressed section 411 of the lead 40 has the following value. That is, the surface area Sa of the pressed section 411 of the lead 40 indicates the sum (total) of the surface areas of the pressed sections 411 of the plurality of leads 40. In the example illustrated in FIG. 2, two through-holes extending in the axial direction are provided inside the elastic body 50, and each of the two through-holes accommodates a corresponding one of the two leads 40 (particularly, two covered section 41). Therefore, in the example illustrated in FIG. 2, the sum of the surface areas of the pressed sections 411 of the two covered sections 41 is the "surface area Sa of the pressed section 411 of the lead 40".

In the example illustrated in FIG. 2, "La" denotes a length (length in the axial direction) (unit: [mm]) of the pressed section 411 of the lead 40. When an outer diameter (circumferential length) of each lead 40 is denoted as "outer diameter Do (unit: [mm])", and the number of leads 40 accommodated in the elastic body 50 is denoted as "number Nm", the above-described surface area Sa can be expressed as follows. That is, the surface area Sa of the pressed section 411 can be expressed as "Sa=Do×La×Nm" using the outer diameter Do of each lead 40, the number Nm of the leads 40, and the length La of the pressed section 411. Note that the surface area Sa will be described below without the units. Similarly, the "diameter Da of the unswaged section 52", the "diameter Db of the swaged section 51", and the "pressure q produced when swaged by the unit length" will be described without the units.

(Distance Between Front End Surface of Elastic Body and Lead Retaining Portion)

As illustrated in FIG. 2, the lead retaining portion 32 that crimps and retains the lead 40 is provided at the rear end of the terminal fitting 30, that is, the terminal fitting 30 includes the lead retaining portion 32 at the rear end in the axial direction. Specifically, the lead retaining portion 32 of the terminal fitting 30 crimps and retains the uncovered section 42 (metal wire) of the lead 40. Then, the lead retaining portion 32 of the terminal fitting 30 is disposed adjacent to the front end relative to the elastic body 50 in the axial direction, that is, the lead retaining portion 32 is disposed adjacent to the front end relative to the front end surface 53 of the elastic body 50 in the axial direction. For example, at least a part of the covered section 41 of the lead 40 is not accommodated in the through-hole of the elastic body 50 and protrudes toward the front end relative to the elastic body 50 (front end surface 53 of the elastic body 50).

In particular, in the gas sensor 1, the lead retaining portion 32 is disposed at a position apart from the front end surface 53 of the elastic body 50 by a predetermined distance in the axial direction, and in the example illustrated in FIG. 2, a distance Li (unit: [mm]) is provided between the front end surface 53 of the elastic body 50 and the lead retaining portion 32. Note that, as with the "surface area Sa", the "diameter Da", the "diameter Db", and the "pressure q produced when swaged by the unit length", the "distance Li between the front end surface 53 of the elastic body 50 and the lead retaining portion 32 in the axial direction" will be described below without the units.

In the example illustrated in FIG. 2, "Li" denotes the distance between the front end surface 53 of the elastic body 50 and the lead retaining portion 32, and denotes particularly a length of the distance in the axial direction. In the gas sensor 1 illustrated in FIG. 2, the length (distance Li in FIG. 2) between the front end surface 53 of the elastic body 50 and the lead retaining portion 32 in the axial direction is greater than or equal to "0.1 mm". That is, in the gas sensor 1, the lead retaining portion 32 is disposed at a position 0.1 mm or more apart from the front end surface 53 (end surface of the front end) of the elastic body 50 in the axial direction.

As described above, in the gas sensor 1, the number of the diameter-reduced portions 221 provided in the tubular body 20 to fix the elastic body 50 to the tubular body 20 (outer tube 22) is "one". Therefore, the gas sensor 1 can reduce the length of the elastic body 50 in the axial direction as compared with the conventional gas sensor in which "two" diameter-reduced portions for fixing the elastic body to the tubular body are provided in the tubular body at a predetermined interval". That is, in the conventional gas sensor in which the "two" diameter-reduced portions are provided at the predetermined interval in the axial direction, the elastic body needs to extend in the axial direction from the open end at the rear end of the tubular body to at least a diameter-reduced portion located adjacent to the front end of the tubular body of the "two" diameter-reduced portions. On the other hand, in the gas sensor 1, the elastic body 50 only needs to extend from the open end at the rear end of the tubular body 20 to the "one" diameter-reduced portion 221. Therefore, the gas sensor 1 in which the "one" diameter-reduced portion 221 is provided at the rear end of the tubular body 20 can reduce the length of the elastic body 50 in the axial direction as compared with the conventional gas sensor in which the "two" diameter-reduced portions are provided at the predetermined interval in the axial direction".

Therefore, even in a case where the length of the entire gas sensor 1 in the axial direction is reduced (shortened), the gas sensor 1 can make the distance between the elastic body 50 that seals the open end at the rear end the tubular body 20 and the front end of the gas sensor 1 long enough. That is, even in a case where the gas sensor 1 is shortened as a whole, the gas sensor 1 can make the distance between the elastic body 50 and the heat source located at the front end of the gas sensor 1 long enough. Therefore, even in a case where the gas sensor 1 is shortened as a whole, the gas sensor 1 can produce an effect of preventing, by making the distance between the elastic body 50 and the heat source long enough, the occurrence of a situation in which the elastic body 50 is exposed to a high temperature to suffer erosion.

Further, in the gas sensor 1, the lead retaining portion 32 of the terminal fitting 30 is not in the through-hole of the elastic body 50, and specifically, the lead retaining portion 32 is apart from the front end surface 53 (end surface of the front end) of the elastic body 50 by 0.1 mm or more in the axial direction.

Therefore, in the gas sensor 1, the lead retaining portion 32 of the terminal fitting 30 neither comes into contact with the inner surface of the through-hole of the elastic body 50 nor blocks the through-hole of the elastic body 50. That is, the gas sensor 1 can produce an effect of preventing the lead retaining portion 32 from coming into contact with the inner surface of the through-hole of the elastic body 50 and preventing the lead retaining portion 32 from blocking the through-hole of the elastic body 50.

(Size or the Like of Each Member)

Here, in a case where the number of the diameter-reduced portions 221 for fixing the elastic body 50 to the tubular body 20 is "one", it may be difficult for the elastic body 50 (particular, the swaged section 51) to restrict the movement of the lead 40 in the axial direction. That is, in a case where the number of the diameter-reduced portions 221 is one, the lead 40 may easily move in the axial direction. Then, as the lead 40 easily moves in the axial direction, the terminal fitting 30 crimped to the lead 40 in the lead retaining portion 32 also easily moves in the axial direction, and the electrical connection between the terminal fitting 30 and the element electrode of the sensor element 10 is easily lost (easily interrupted). Therefore, in a case where the number of the diameter-reduced portions 221 is one, contact misalignment (interruption of the electrical connection between the terminal fitting 30 and the element electrode of the sensor element 10) may easily occur in the gas sensor 1.

Therefore, adjusting the size or the like of each member to satisfy the following expression (1) allows the gas sensor 1 to prevent the occurrence of contact misalignment. That is, the gas sensor 1 including each member whose size or the like has been adjusted to satisfy the expression (1) causes the elastic body 50 (particularly, only one swaged section 51 corresponding to only one diameter-reduced portion 221) to restrict the movement of the lead 40 in the axial direction to prevent the occurrence of contact misalignment. Specifically, in the gas sensor 1, the diameter Da of the unswaged section 52, the diameter Db of the swaged section 51, the surface area Sa of the pressed section 411 of the lead 40, the coefficient of static friction $\mu$, and the pressure q produced when swaged by the unit length satisfy the expression (1). That is, the gas sensor 1 satisfies:

$$(Da - Db) \times Sa > Fc/(\mu \times q). \qquad \text{expression (1)}$$

As described above, the pressed section 411 of the lead 40 is a section of the covered section 41 of the lead 40 accommodated in the through-hole in the swaged section 51 of the elastic body 50. In a case where the covered section 41 of each of the plurality of leads 40 is accommodated in a corresponding one of the plurality of through-holes of the elastic body 50, the surface area Sa is the sum of the surface areas of the pressed sections 411 of the plurality of leads 40. Although details will be described later, "Fc" in the expression (1) denotes a load in the axial direction that interrupts the electrical connection between the terminal fitting 30 and the element electrode of the sensor element 10, and is a load in the axial direction whose magnitude (value) can be obtained in advance through a test or the like.

The inventors of the present invention have verified that the elastic body 50 (particularly, the swaged section 51) restricts the movement of the lead 40 in the axial direction as follows. That is, swaging the elastic body 50 from the periphery of the elastic body 50 accommodating the covered section 41 of the lead 40 in the through-hole formed inside the elastic body 50 causes a radial force (vertical drag Fn) to act on the lead 40 (particularly, the pressed section 411 of the covered section 41). As a result, a static frictional force Ff proportional to the coefficient of static friction u between the elastic body 50 and the covered section 41 (particularly, the pressed section 411), and the vertical drag Fn is generated against the movement of the lead 40 in the axial direction. That is, "Ff=μ×Fn" holds. The static frictional force Ff prevents the lead 40 from moving in the axial direction.

The vertical drag Fn is proportional to the "pressure q produced when swaged by the unit length", a "difference between the diameter Da of the unswaged section 52 and the diameter Db of the swaged section 51", and the "surface area Sa of the pressed section 411" described above. That is, "Fn=(Da−Db)×Sa×q" holds. As described above, the "pressure q produced when swaged by the unit length" indicates pressure per unit area applied to the covered section 41 by the elastic body 50 when the elastic body 50 is radially swaged by the unit length. Further, the "surface area Sa of the pressed section 411" is the surface area of the "section accommodated in the swaged section 51 (more precisely, the through-hole in the swaged section 51) of the elastic body 50" of the covered section 41. Furthermore, in a case where the covered section 41 of each of the plurality of leads 40 is accommodated in a corresponding one of the plurality of through-holes provided inside the elastic body 50, the "surface area Sa of the pressed section 411" is expressed as follows. That is, it is expressed as "Sa=Do×La×Nm" using the outer diameter (circumferential length) Do of each of the plurality of leads 40, the length La of the swaged section 51 in the axial direction, and the number Nm of the plurality of leads 40.

As described above, since "Ff=μ×Fn" and "Fn=(Da−Db)×Sa×q" hold, the static frictional force Ff between the elastic body 50 and the covered section 41 is expressed as "Ff=μ×(Da−Db)×Sa×q".

Then, the inventors of the present invention have verified the magnitude of the load in the axial direction that causes contact misalignment by conducting a test of pulling the lead 40 in the axial direction on the gas sensor in which the terminal fitting 30 and the element electrode of the sensor element 10 are electrically connected to each other. As a result, the inventors of the present invention have verified that (the magnitude of) the load in the axial direction that causes contact misalignment is (the magnitude of) the load Fc in the axial direction. That is, the inventors of the present invention have verified that the magnitude of the force (load) to pull the lead 40 in the axial direction when contact misalignment occurs (that is, the electrical connection between the terminal fitting 30 and the element electrode of the sensor element 10 is interrupted) is the magnitude of the load Fc in the axial direction.

It is therefore possible to prevent the occurrence of contact misalignment by making (the magnitude of) the static frictional force Ff larger than (the magnitude of) the load Fc in the axial direction. As described above, since "Ff=μ×(Da−Db)×Sa×q" holds, it is possible to prevent the occurrence of contact misalignment by satisfying "μ×(Da−Db)×Sa×q>Fc". The relational expression is transformed into "(Da−Db)×Sa>Fc/(μ×q)" given as the expression (1).

Therefore, the gas sensor 1 in which the diameter Da of the unswaged section 52, the diameter Db of the swaged section 51, the surface area Sa of the pressed section 411, the coefficient of static friction μ, and the pressure q produced when swaged by the unit length satisfy the expression (1) can prevent the occurrence of contact misalignment.

Furthermore, since the number of the diameter-reduced portions 221 provided in the tubular body 20 is one, the gas sensor 1 can reduce the number of items whose dimensions are to be managed and reduce the number of man-hours required for inspection and the inspection cost as compared with the conventional gas sensor in which two diameter-reduced portions 221 are provided in the tubular body 20 at a predetermined interval. As described above, since the elastic body 50 of the gas sensor 1 can be shortened as compared with the conventional gas sensor, the material cost of the elastic body 50 can be reduced, and the number of choices of the material of the elastic body 50 can be further increased to allow the selection of the most suitable material.

Note that the inventors of the present invention have verified that "the magnitude of the load Fc in the axial direction that interrupts the electrical connection between terminal fitting 30 and the element electrode of the sensor element 10" is, for example, "150 [N]" or "180 [N]" through the above-described test. For the gas sensor according to the present invention, "the magnitude of the load Fc in the axial direction that interrupts the electrical connection between the terminal fitting 30 and the element electrode of the sensor element 10", however, need not necessarily be "150" or "180". "Fc" of the gas sensor according to the present invention is determined as appropriate in accordance with the size, shape, material, and the like of each member of the gas sensor.

Further, the "coefficient of static friction u between the elastic body 50 and the covered section 41 of the lead 40" can be obtained in advance in accordance with the respective materials (properties of materials) of the elastic body 50 and the covered section 41 of the lead 40. Similarly, the "pressure q produced when swaged by the unit length" can be obtained in advance in accordance with the material of the elastic body 50. Therefore, the value of "μ×q" in the expression (1) can be obtained in advance in accordance with the respective materials of the elastic body 50 and the covered section 41 of the lead 40. For example, in a case where fluoro-rubber was used as the material of the elastic body 50, and fluoro-resin was used as the material of the covered section 41 of the lead 40, the value of "μ×q" is "1.7" or "1.1". For the gas sensor according to the present invention, the value of "μ×q", however, need not necessarily be "1.7" or "1.1". The value of "μ×q" for the gas sensor according to the present invention can be obtained in advance in accordance with the respective materials (properties of materials) of the elastic body and the covered section of the lead.

Furthermore, in the gas sensor 1, the diameter Da of the unswaged section 52 and the diameter Db of the swaged section 51 satisfy the following expression (2). That is, the gas sensor 1 satisfies:

$$Db/Da \geq 0.5. \qquad \text{expression (2)}$$

That is, in the gas sensor 1, the diameter Db of the swaged section 51 is greater than or equal to 50% of the diameter Da of the unswaged section 52.

The inventors of the present invention have verified that the following problem occurs when the diameter Db of the swaged section 51 is less than 50% of the diameter Da of the unswaged section 52. That is, it has been verified that a gap is generated between the tubular body 20 and the elastic body 50, which causes a problem such as deterioration in the sealing performance of the elastic body 50 (the airtightness in the tubular body 20 achieved by the elastic body 50). Therefore, when the diameter Db of the swaged section 51 is set greater than or equal to 50% of the diameter Da of the unswaged section 52, the gas sensor 1 can produce an effect of maintaining the sealing performance of the elastic body 50 high enough to maintain or improve the accuracy of gas concentration detection.

<Consideration of how Lead Retaining Portion is Accom-modated>

As described above, in the gas sensor according to the present invention, the lead retaining portion (section that crimps and retains the lead) of the terminal fitting is not in the elastic body, and specifically, the lead retaining portion is apart from the front end surface of the elastic body by 0.1 mm or more in the axial direction. For example, in the gas sensor 1, the lead retaining portion 32 is not in the through-hole of the elastic body 50, and specifically, the lead retaining portion 32 is apart from the front end surface 53 (end surface of the front end) of the elastic body 50 by 0.1 mm or more in the axial direction.

Here, in the gas sensor 1 illustrated in FIGS. 1 and 2, the lead retaining portion 32 is exposed to the internal space of the tubular body 20 (outer tube 22). For example, while the element contact portion 31 located at the front end of the terminal fitting 30 is accommodated inside the ceramic housing 60, the lead retaining portion 32 located at the rear end of the terminal fitting 30 is exposed to the internal space of the tubular body 20 on the rear end of the ceramic housing 60. In the gas sensor according to the present invention, the lead retaining portion of the terminal fitting, however, need not necessarily be exposed to the internal space of the tubular body. In the gas sensor according to the present invention, the lead retaining portion may be accommodated in the tubular body with the lead retaining portion covered with a member other than the elastic body. In the gas sensor according to the present invention, the lead retaining portion of the terminal fitting only needs to be apart from the front end surface of the elastic body by 0.1 mm or more in the axial direction. In the gas sensor according to the present invention, whether the lead retaining portion of the terminal fitting is accommodated in the tubular body with the lead retaining portion exposed or accommodated in the tubular body with the lead retaining portion covered with a member other than the elastic body is determined as appropriate in accordance with the application, use environment, and the like of the gas sensor. Hereinafter, a gas sensor according to one aspect of the present invention in which the "lead retaining portion of the terminal fitting is accommodated in the tubular body with the lead retaining portion covered with a member other than the elastic body" will be described with reference to FIG. 3.

Figure 3:
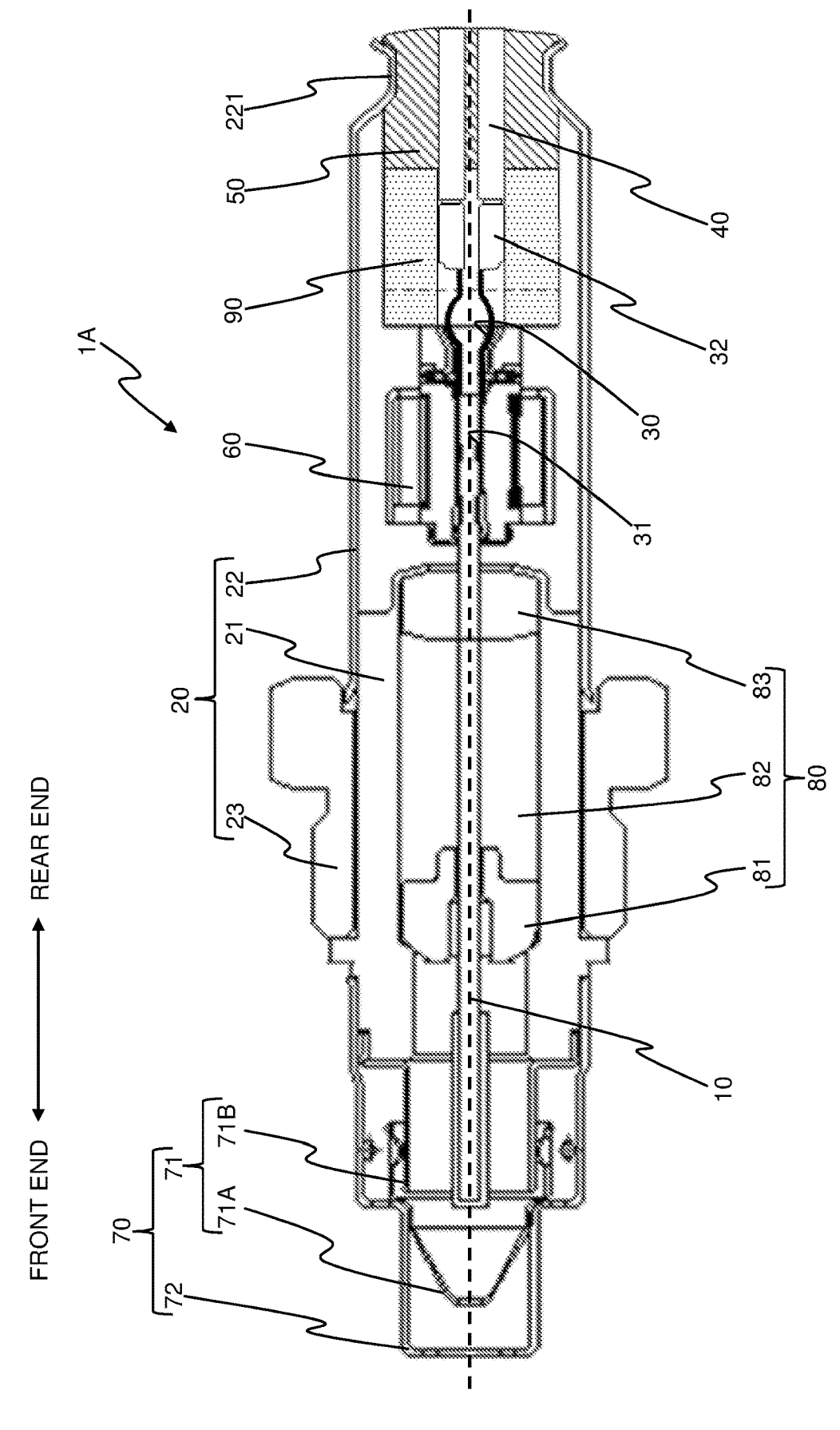
FIG. 3 is a schematic cross-sectional view schematically illustrating an example of a configuration of a gas sensor according to a first modification.

FIG. 3 is a schematic cross-sectional view schematically illustrating an example of a configuration of a gas sensor 1A according to a first modification. That is, FIG. 3 schematically illustrates a configuration of a cross section of the gas sensor 1A parallel to the longitudinal axis (axis line, line along the left-right direction of drawing) and in contact with the axis. The gas sensor 1A is an example of the "gas sensor" of the present invention, and is a gas sensor capable of detecting a concentration of a specific gas (specific gas concentration) such as oxygen or $NO_x$ in the gas being measured such as an exhaust gas of an automobile. The gas sensor 1A is the same as gas sensor 1 except that the gas sensor 1A further includes a spacer 90 in addition to the configuration of the gas sensor 1, so that no detailed descrip-tion of the configuration other than the spacer 90 will be given below.

In the example in FIG. 3, the gas sensor 1A is disposed such that the front end of the gas sensor 1A faces left, and the rear end of the gas sensor 1A faces right. That is, the left-right direction of FIG. 3 corresponds to the longitudinal direction (axial direction). As with the gas sensor 1, the gas sensor 1A includes the sensor element 10, the tubular body 20, the terminal fitting 30, the lead 40, the elastic body 50, the ceramic housing 60, and the protective cover 70, and the gas sensor 1A further includes the spacer 90.

(Spacer)

The spacer 90 is an example of the "spacer" of the present invention. The spacer 90 is disposed between the ceramic housing 60 and the elastic body 50 in the axial direction of the gas sensor 1A (sensor element 10). That is, the spacer 90 is sandwiched (interposed) between the ceramic housing 60 and the elastic body 50 inside the tubular body 20 (outer tube 22). For example, the spacer 90 is restricted in movement in axial direction (particularly, movement toward the front end) by the ceramic housing 60.

The lead 40 is inserted into the spacer 90 illustrated in FIG. 3. Specifically, the lead 40 and the terminal fitting 30 (particularly, the lead retaining portion 32 that crimps and retains the lead 40) are accommodated inside the spacer 90. For example, a through-hole extending in the axial direction is provided inside the spacer 90. As with the inside of the elastic body 50, a plurality of through-holes extending in the axial direction may be provided inside the spacer 90. The lead 40 and the lead retaining portion 32 of the terminal fitting 30 are accommodated (inserted) in the through-hole provided inside the spacer 90. For example, the plurality of leads 40 and the plurality of lead retaining portions 32 are each accommodated (inserted) in a corresponding one of the plurality of through-holes provided inside the spacer 90. FIG. 3 illustrates an example in which two through-holes are provided inside the spacer 90, and two leads 40 and two lead retaining portions 32 are each accommodated in a corre-sponding one of the two through-holes. Then, in the gas sensor 1A, the lead retaining portion 32 and the lead 40 are electrically connected to each other in the spacer 90.

The spacer 90 includes, for example, a heat-resistant material. When the spacer 90 includes a heat-resistant mate-rial, it is possible to prevent the occurrence of a situation in which the spacer 90 disposed adjacent to the front end relative to the elastic body 50 in the axial direction is eroded by heat generated from the heat source located at the front end of the gas sensor 1A. For example, when the spacer 90 is interposed between the elastic body 50 and the ceramic housing 60, it is possible to prevent an excessive rise in temperature of the elastic body 50 while the gas sensor 1A is in use or the like. That is, from the viewpoint of reducing heat transfer to the elastic body 50, the spacer 90 is desirably low in thermal conductivity. However, while the rise in temperature of the elastic body 50 is suppressed by the spacer 90, the temperature of the spacer 90 becomes high, so that the spacer 90 itself needs to have sufficient heat resis-tance. Therefore, when the spacer 90 includes a heat-resistant material, it is possible to prevent the occurrence of a situation in which the spacer 90 itself is eroded by heat generated from the heat source while reducing heat transfer from the heat source to the elastic body 50.

Note that FIG. 3 illustrates an example in which the spacer 90 is a single member, but the spacer 90 may include a plurality of components (constituent members). For example, the spacer 90 may include a spacer front end section disposed at the front end in the axial direction and a spacer rear end section disposed at the rear end. That is, the spacer 90 may have a multi-stage configuration (for example, a two-stage configuration) including the spacer front end section and the spacer rear end section.

In a case where the spacer 90 is used to suppress the rise in temperature of the elastic body 50 while the gas sensor 1A is in use, the spacer front end section and the spacer rear end section described above may be configured as follows. That is, as the properties of material of the spacer front end section disposed at the front end in the axial direction, ceramics higher in melting point than resin is selected from the viewpoint of having more excellent heat resistance than the spacer rear end section. Preferably, ceramics having a thermal conductivity of 32 W/m·K or less, which is suitable also from the viewpoint of heat insulation in addition to heat resistance, is selected, and more preferably, alumina (thermal conductivity: 32 W/m·K) or steatite (thermal conductivity: 2 W/m·K) is selected. On the other hand, as the properties of material of the spacer rear end section that is in contact with the elastic body 50, resin is selected rather than ceramics or the like from the viewpoint of having low thermal conductivity. Preferably, the resin used for the spacer rear end section is polytetrafluoroethylene (PTFE, melting point: 327° C.)) or perfluoroalkoxy alkane (PFA, melting point: 310° C., both of which are fluoro-resin. Such resins have not only low thermal conductivity but also higher heat resistance than the rubber elastic body 50. For example, PTFE has a thermal conductivity of 0.2 W/m·K, and a continuous maximum use temperature (maximum temperature in a case of continuous use at the maximum temperature) of 260° C.

In the gas sensor 1A illustrated in FIG. 3, the tubular body 20 (outer tube 22) covers the periphery of the rear end of the sensor element 10, the periphery of the ceramic housing 60 (terminal fitting 30), and the periphery of the spacer 90. That is, in the example illustrated in FIG. 3, the sensor element 10, the annular-fitting component 80 for fixing fitted around the sensor element 10, the ceramic housing 60 (terminal fitting 30), and the spacer 90 are accommodated inside the tubular body 20, and the open end at the rear end of the tubular body 20 is sealed by the elastic body 50.

Further, in the gas sensor 1A, the lead 40 is inserted into, for example, a through-hole (not illustrated) continuously provided in the elastic body 50 and the spacer 90, and the front end portion (uncovered section 42) of the lead 40 is crimped and fixed to the lead retaining portion 32 of the terminal fitting 30. Note that although FIG. 3 illustrates an example in which there are two terminal fittings 30 and two leads 40, this is merely for the sake of simplicity of illustration. In practice, the gas sensor 1A includes the terminal fittings 30 and the leads 40 as many as necessary for the above-described electrical connection.

The lead retaining portion 32 of the terminal fitting 30 illustrated in FIG. 3 is accommodated in the spacer 90, that is, in the gas sensor 1A illustrated in FIG. 3, the lead retaining portion 32 and the lead 40 are electrically connected to each other in the spacer 90. Further, the element contact portion 31 of the terminal fitting 30 is accommodated in the ceramic housing 60.

As described above, the gas sensor 1A illustrated in FIG. 3 further includes the spacer 90 in addition to the configuration of the gas sensor 1 described with reference to FIGS. 1 and 2. That is, the gas sensor 1A includes the ceramic housing 60 in which the "element electrode of the sensor element 10 and the front end section (element contact portion 31) of the terminal fitting 30 electrically connected to the element electrode are accommodated" and the spacer 90. In the gas sensor 1A, the spacer 90 is disposed between the ceramic housing 60 and the elastic body 50 in the axial direction. That is, in the gas sensor 1A, the elastic body 50 is disposed adjacent to the rear end in the axial direction relative to the ceramic housing 60 and the spacer 90.

Therefore, the gas sensor 1A can produce an effect of reducing transfer of heat generated from the heat source located at the front end of the gas sensor 1A to the elastic body 50 more effectively by means of the ceramic housing 60 and the spacer 90. Note that the spacer 90 disposed adjacent to the front end relative to the elastic body 50 in the axial direction preferably includes a heat-resistant material. When the spacer 90 includes a heat-resistant material, it is possible to prevent the occurrence of a situation in which the spacer 90 disposed adjacent to the front end relative to the elastic body 50 in the axial direction is eroded by heat generated from the above-described heat source.

In the gas sensor 1A, the lead retaining portion 32 of the terminal fitting 30 is disposed inside the spacer 90. Therefore, the gas sensor 1A can produce an effect of preventing the lead retaining portion 32 from coming into contact with the elastic body 50 or closing the through-hole of the elastic body 50 more efficiently.

Note that the gas sensor 1A has the same configuration as the configuration of the gas sensor 1 except that the spacer 90 is provided. That is, as with the gas sensor 1, the gas sensor 1A includes the sensor element 10, the tubular body 20, the terminal fitting 30, the lead 40, and the elastic body 50. In the gas sensor 1A, the lead retaining portion 32 that crimps and retains the lead 40 (particularly, the uncovered section 42 of the lead 40) is provided at the rear end of the terminal fitting 30, and one diameter-reduced portion 221 that swages a part of the elastic body 50 from the periphery of the elastic body 50 is provided in the tubular body 20. Therefore, even in a case where the length of the entire gas sensor 1A in the axial direction is reduced (shortened), the gas sensor 1A can make the distance between the elastic body 50 that seals the open end at the rear end of the tubular body 20 and the front end of the gas sensor 1A long enough. That is, even in a case where the gas sensor 1A is shortened as a whole, the gas sensor 1A can make the distance between the elastic body 50 and the heat source located at the front end of the gas sensor 1A long enough. Therefore, even in a case where the gas sensor 1A is shortened as a whole, the gas sensor 1A can produce an effect of preventing, by making the distance between the elastic body 50 and the heat source long enough, the occurrence of a situation in which the elastic body 50 is exposed to a high temperature to suffer erosion.

Further, in the gas sensor 1A, the lead retaining portion 32 is not in the through-hole of the elastic body 50, and specifically, the lead retaining portion 32 is apart from the front end surface 53 of the elastic body 50 by 0.1 mm or more in the axial direction. Therefore, in the gas sensor 1A, the lead retaining portion 32 neither comes into contact with the inner surface of the through-hole of the elastic body 50 nor blocks the through-hole. That is, the gas sensor 1A can produce an effect of preventing the lead retaining portion 32 from coming into contact with the inner surface of the through-hole of the elastic body 50 and preventing the lead retaining portion 32 from blocking the through-hole.

Furthermore, in the gas sensor 1A, the diameter Da of the unswaged section 52, the diameter Db of the swaged section 51, the surface area Sa of the pressed section 411 of the lead 40, the coefficient of static friction μ, and the pressure q produced when swaged by the unit length satisfy the expression (1). That is, the gas sensor 1A satisfies:

$$(Da - Db) \times Sa > Fc/(\mu \times q). \qquad \text{expression (1)}$$

As described above, in a case where the diameter Da, the diameter Db, the surface area Sa, the coefficient of static friction μ, and the pressure q produced when swaged by the unit length satisfy the expression (1), the elastic body 50 effectively restricts the movement of the lead 40 in the axial direction, so that the occurrence of contact misalignment can be prevented. The gas sensor 1A can therefore prevent the occurrence of contact misalignment.

Furthermore, since the number of the diameter-reduced portions 221 provided in the tubular body 20 is one, the gas sensor 1A can reduce the number of items whose dimensions are to be managed and reduce the number of man-hours required for inspection and the inspection cost as compared with the conventional gas sensor in which two diameter-reduced portions 221 are provided in the tubular body 20 at a predetermined interval. As described above, since the elastic body 50 of the gas sensor 1A can be shortened as compared with the conventional gas sensor, the material cost of the elastic body 50 can be reduced, and the number of choices of the material of the elastic body 50 can be further increased to allow the selection of the most suitable material.

Here, also in the gas sensor 1A, as in the gas sensor 1, the diameter Da of the unswaged section 52 and the diameter Db of the swaged section 51 satisfy the following expression (2). That is, the gas sensor 1A satisfies:

$$Db/Da \geq 0.5. \qquad \text{expression (2)}$$

That is, in the gas sensor 1A, the diameter Db of the swaged section 51 is greater than or equal to 50% of the diameter Da of the unswaged section 52.

As described above, the inventors of the present invention have verified that when the diameter Db of the swaged section 51 is less than 50% of the diameter Da of the unswaged section 52, a problem such as deterioration in the sealing performance of the elastic body 50 occurs. Therefore, when the diameter Db of the swaged section 51 is set greater than or equal to 50% of the diameter Da of the unswaged section 52, the gas sensor 1A can produce an effect of maintaining the sealing performance of the elastic body 50 high enough to maintain or improve the accuracy of gas concentration detection.

Features

As described above, the gas sensor 1 and the gas sensor 1A according to the present embodiment each include the sensor element 10, the tubular body 20, the terminal fitting 30, the lead 40, and the elastic body 50. The sensor element 10 extends in the axial direction, includes the detection portion at the front end and the element electrode at the rear end. The tubular body 20 is a tubular (for example, a cylindrical) member, and the sensor element 10 and the terminal fitting 30 are arranged inside the tubular body. The terminal fitting 30 extends in the axial direction, the front end (specifically, the element contact portion 31) of terminal fitting 30 is electrically connected to the element electrode of the sensor element 10, and the lead retaining portion 32 that crimps and retains the lead 40 is provided at the rear end of the terminal fitting 30. The lead 40 is electrically connected to the rear end (specifically, the lead retaining portion 32) of the terminal fitting 30, and extends outward from the open end at the rear end of the tubular body 20. The elastic body 50 is disposed to seal the open end at the rear end of the tubular body 20, the through-hole extending in the axial direction is provided in the elastic body 50, and the covered section 41 of the lead 40 is accommodated in the through-hole.

In each of the gas sensor 1 and the gas sensor 1A, "one" diameter-reduced portion 221 that swages a part of the elastic body 50 from the periphery of the elastic body 50 is provided in the tubular body 20. Therefore, in each of the gas sensor 1 and the gas sensor 1A, the length of the elastic body 50 in the axial direction can be reduced as compared with the "conventional gas sensor in which "two" diameter-reduced portions 221 for fixing the elastic body 50 to the tubular body 20 are provided in the tubular body 20 at a predetermined interval". Therefore, even in a case where the length of each of the gas sensor 1 and the gas sensor 1A is shortened, the gas sensor can make the distance between the elastic body 50 that seals the open end at the rear end of the tubular body 20 and the front end of the gas sensor long enough. That is, even in a case where each of the gas sensor 1 and the gas sensor 1A is shortened as a whole, the gas sensor can make the distance between the elastic body 50 and the heat source located at the front end of the gas sensor long enough. Therefore, even in a case where each of the gas sensor 1 and the gas sensor 1A is shortened as a whole, the gas sensor can produce an effect of preventing, by making the distance between the elastic body 50 and the heat source long enough, the occurrence of a situation in which the elastic body 50 is exposed to a high temperature to suffer erosion.

In each of the gas sensor 1 and the gas sensor 1A, the lead retaining portion 32 is apart from the front end surface 53 (end surface of the front end) of the elastic body 50 by 0.1 mm or more in the axial direction. Therefore, in each of the gas sensor 1 and the gas sensor 1A, the lead retaining portion 32 neither comes into contact with the inner surface of the through-hole of the elastic body 50 nor blocks the through-hole. That is, the gas sensor 1 and the gas sensor 1A can each produce an effect of preventing the lead retaining portion 32 from coming into contact with the inner surface of the through-hole of the elastic body 50 and preventing the lead retaining portion 32 from blocking the through-hole.

In each of the gas sensor 1 and the gas sensor 1A, the diameter Da of the unswaged section 52, the diameter Db of the swaged section 51, the surface area Sa of the pressed section 411 of the lead 40, the coefficient of static friction μ, and the pressure q produced when swaged by the unit length satisfy the expression (1). That is, the gas sensor 1 and the gas sensor 1A each satisfy:

$$(Da - Db) \times Sa > Fc/(\mu \times q). \qquad \text{expression (1)}$$

As described above, in a case where the diameter Da, the diameter Db, the surface area Sa, the coefficient of static friction μ, and the pressure q produced when swaged by the unit length satisfy the expression (1), the elastic body 50 effectively restricts the movement of the lead 40 in the axial direction, so that the occurrence of contact misalignment can be prevented. The gas sensor 1 and the gas sensor 1A can therefore each prevent the occurrence of contact misalignment.

Furthermore, since the number of the diameter-reduced portions 221 provided in the tubular body 20 is one, the gas sensor 1 and the gas sensor 1A each produce the following effects as compared with the conventional gas sensor in which "two diameter-reduced portions 221 are provided in the tubular body 20 at an interval". That is, the gas sensor 1 and the gas sensor 1A can each reduce the number of items whose dimensions are to be managed, and can reduce the number of man-hours required for inspection and the inspection cost. As described above, the elastic body 50 of each of the gas sensor 1 and the gas sensor 1A can be shortened as compared with the conventional gas sensor. Therefore, the material cost of the elastic body 50 of each of the gas sensor 1 and the gas sensor 1A can be reduced, and further, the number of choices of the material of the elastic body 50 can be increased to allow the selection of the most suitable material.

Modification

Although the embodiment of the present invention has been described above, the description of the embodiment given above is merely an example of the present invention in all respects. Various improvements and modifications may be made to the above-described embodiment. With respect to each component of the above-described embodiment, omission, replacement, and addition of the component may be made as appropriate. Further, the shape and dimension of each component of the above-described embodiment may be changed as appropriate in accordance with the embodiment. For example, the following modifications are possible. Note that, in the following description, the same components as in the above-described embodiment are denoted by the same reference numerals, and the description of the same points as in the above-described embodiment is omitted as appropriate. The following modifications can be combined as appropriate.

FIG. 3 illustrates an example of the spacer 90 of which the end surface of the front end (front end surface) in the axial direction is flat. For the gas sensor according to the present invention, the front end surface of the spacer 90, however, need not necessarily be flat. The spacer 90 that is in contact with the ceramic housing 60 (particularly, an end surface of the rear end (rear end surface) of the ceramic housing 60) at the front end surface may be in contact with the ceramic housing 60 only at a part of the front end surface. For example, one or a plurality of recesses may be provided on the front end surface of the spacer 90, and the spacer 90 may be in contact with the ceramic housing 60 (particularly, the rear end surface of the ceramic housing 60) at a section excluding the one or the plurality of recesses. Further, one or a plurality of protrusions may be provided on the front end surface of the spacer 90, and the spacer 90 may be in contact with the ceramic housing 60 only at the apex of the one or the plurality of protrusions (the apex of each of the plurality of protrusions in a case where the plurality of protrusions are provided).

The gas sensor according to the present invention can produce the following effect by bringing only a part of the front end surface, not all the front end surface, of the spacer 90 into contact with the ceramic housing 60 (particularly, the rear end surface of the ceramic housing 60). That is, the gas sensor according to the present invention can produce an effect of reducing heat transfer from the ceramic housing 60 to the spacer 90 and further to the elastic body 50. For example, in order to reduce thermal deterioration of the elastic body 50 while making the strength of the spacer 90 high enough, in the spacer 90 of the gas sensor according to the present invention, at least either of one or a plurality of recesses and one or a plurality of protrusions may be provided on the front end surface. The spacer 90 in which at least either of one or a plurality of recesses and one or a plurality of protrusions is provided on the front end surface is in contact with the ceramic housing 60 (particularly, the rear end surface of the ceramic housing 60) at a part of the front end surface rather than all the front end surface.

Example

In order to verify the effects of the present invention (particularly, capability of preventing contact misalignment), the inventors of the present invention prepared the following gas sensors according to levels 1 to 8 and conducted a vibration test to verify the above-described effects. In the vibration test, the acceleration was fixed at 40 G, and the frequency of the sine wave (vibration) was changed from 1000 Hz to 3300 Hz at a sweep rate of 0.057 oct/min. These vibrations were input to each of the gas sensors according to the levels 1 to 8 fixed to a base, and whether or not contact misalignment occurs was checked. The present invention, however, is not limited to the following examples (levels).

TABLE 1

| Level | Da | Db | Sa | $\mu \times q$ | Fc | $(Da - Db) \times Sa$ | $Fc/(\mu \times q)$ | Contact misalignment |
|-------|----|----|-----|-----|-----|-----|--------|------|
| 1 | 11 | 9.4 | 60 | 1.7 | 150 | 96 | 89.45 | Pass |
| 2 | 11 | 9.4 | 60 | 1.1 | 150 | 96 | 136.65 | Fail |
| 3 | 11 | 9.4 | 100 | 1.7 | 150 | 160 | 89.45 | Pass |
| 4 | 11 | 9.4 | 100 | 1.1 | 150 | 160 | 136.65 | Pass |
| 5 | 11 | 9.4 | 60 | 1.7 | 180 | 96 | 107.33 | Fail |
| 6 | 11 | 9.4 | 60 | 1.1 | 180 | 96 | 163.98 | Fail |
| 7 | 11 | 9.4 | 100 | 1.7 | 180 | 160 | 107.33 | Pass |
| 8 | 11 | 9.4 | 100 | 1.1 | 180 | 160 | 163.98 | Fail |

Table 1 shows an outline of the configuration of each gas sensor according to the levels 1 to 8 and results of the vibration test described above. Each of the levels 1 to 8 is a gas sensor including the members illustrated in FIG. 1. The gas sensors according to the levels 1 to 8, however, are different from each other in at least one of the diameter Da of the unswaged section 52, the diameter Db of the swaged section 51, the surface area Sa of the pressed section 411 of the lead 40, the coefficient of static friction $\mu$, or the pressure q produced when swaged by the unit length. In other words, the gas sensors according to the levels 1 to 8 have the same configuration (members) except for the values of the diameter Da, the diameter Db, the surface area Sa, the coefficient of static friction $\mu$, and the pressure q produced when swaged by the unit length.

In Table 1, "Da" denotes the diameter Da of the unswaged section 52 that is a section not swaged by the diameter-reduced portion 221 of the elastic body 50 included in each of the gas sensors according to the levels 1 to 8. In Table 1, "Db" denotes the diameter Db of the swaged section 51 that is a section swaged by the diameter-reduced portion 221 of the elastic body 50 included in each of the gas sensors according to the levels 1 to 8. In Table 1, "Sa" denotes the surface area Sa of the pressed section 411 of the lead 40 included in each of the gas sensors according to the levels 1 to 8. As described above, the pressed section 411 is the "section accommodated in the through-hole of the swaged section 51 of the elastic body 50" of the lead 40 (particularly, the covered section 41). In Table 1, "μ" denotes the coefficient of static friction u between the elastic body 50 and the covered section 41 of the lead 40 included in each of the gas sensors according to the levels 1 to 8. In Table 1, "q" denotes the pressure q per unit area applied to the covered section 41 (particularly, the pressed section 411) of the lead 40 by the elastic body 50 when the elastic body 50 is radially swaged by the unit length by one diameter-reduced portion 221 provided in the tubular body 20. That is, "q" in Table 1 denotes the "pressure q produced when swaged by the unit length" described above. In Table 1, "Fc" denotes the magnitude of the load Fc in the axial direction that interrupts the electrical connection between the element electrode of the sensor element 10 and the terminal fitting 30 included in each of the gas sensors according to the levels 1 to 8. In Table 1, "contact misalignment" indicates a result of the vibration test, and "pass" indicates that no contact misalignment occurred, and "fail" indicates that contact misalignment occurred.

The "coefficient of static friction u between the elastic body 50 and the covered section 41 of the lead 40" can be obtained in advance in accordance with the respective materials (properties of materials) of the elastic body 50 and the covered section 41 of the lead 40. Similarly, the "pressure q produced when swaged by the unit length" can be obtained in advance in accordance with the material of the elastic body 50. Therefore, the value of "μ×q" in Table 1 can be obtained in advance in accordance with the respective materials of the elastic body 50 and the covered section 41 of the lead 40, and was "1.7" or "1.1" in the above-described test. For the gas sensor according to the present invention, the value of "μ×q", however, need not necessarily be "1.7" or "1.1". The value of "μ×q" for the gas sensor according to the present invention can be obtained in advance in accordance with the respective materials (properties of materials) of the elastic body and the covered section of the lead.

The "magnitude of the load Fc in the axial direction that interrupts the electrical connection between the element electrode of the sensor element 10 and the terminal fitting 30" was obtained by conducting the following test on a conventional general gas sensor. Then, the inventors of the present invention conducted a test of pulling a lead in the axial direction on the general gas sensor in which a metal terminal and an element electrode of a sensor element are electrically connected to each other to obtain the magnitude of the load in the axial direction that causes contact misalignment. Through the test, the inventors of the present invention have verified that the "magnitude of the load Fc in the axial direction that interrupts the electrical connection between the element electrode and the metal terminal" is, for example, "150 [N]" or "180 [N]". Therefore, in Table 1, "Fc" is "150" or "180". For the gas sensor according to the present invention, the "magnitude of the load Fc in the axial direction that interrupts the electrical connection between the element electrode of the sensor element 10 and the terminal fitting 30" need not necessarily be "150" or "180". "Fc" of the gas sensor according to the present invention is determined as appropriate in accordance with the size, shape, material, and the like of each member of the gas sensor.

(Matters Verified by Test)

In Table 1, among the gas sensors according to the levels 1 to 8, the gas sensors according to the levels 1, 3, 4, and 7 in which "(Da−Db)×Sa" is greater than "Fc/(μ×q)" had no contact misalignment. On the other hand, contact misalignment occurred in the gas sensors according to the levels 2, 5, 6, and 8. Therefore, the inventors of the present invention have verified the following matters regarding the gas sensor 1 in which the number of the diameter-reduced portions 221 for fixing the elastic body 50 to the tubular body 20 is one, and the elastic body 50 is shortened to make the distance between the lead retaining portion 32 and the front end surface 53 of the elastic body 50 greater than or equal to 0.1 mm. That is, it has been verified that the gas sensor 1 can produce an effect of restricting, by making "(Da−Db)×Sa" greater than "Fc/(μ×q)", the movement of the lead 40 in the axial direction using the above-described static frictional force F to prevent contact misalignment.

REFERENCE SIGNS LIST

1, 1 (A) Gas sensor
10 Sensor element
20 Tubular body
221 Diameter-reduced portion
30 Terminal fitting
31 Element contact portion (front end section of terminal fitting electrically connected to element electrode)
32 Lead retaining portion
40 Lead
41 Covered section
411 Pressed section (section of covered section accommodated in through-hole in swaged section)
50 Elastic body
51 Swaged section
52 Unswaged section
53 Front end surface (end surface of front end of elastic body)
60 Ceramic housing
90 Spacer

The invention claimed is:

1. A gas sensor comprising:

a sensor element extending in an axial direction, the sensor element including a detection portion at a front end and an element electrode at a rear end;

a terminal fitting extending in the axial direction and having a front end electrically connected to the element electrode;

a tubular body in which the sensor element and the terminal fitting are arranged;

a lead electrically connected to a rear end of the terminal fitting and extending outward from an open end at a rear end of the tubular body; and an elastic body disposed to seal the open end, the elastic body having a through-hole extending in the axial direction provided therein, the through-hole accommodating a covered section of the lead, wherein a lead retaining portion that crimps and retains the lead is provided at the rear end of the terminal fitting, one diameter-reduced portion that swages a part of the elastic body from a periphery of the elastic body is provided in the tubular body, the lead retaining portion is apart from an end surface of a front end of the elastic body by 0.1 mm or more in the axial direction, and an expression (1) given below is satisfied:

$$(Da - Db) \times Sa > Fc/(\mu \times q), \qquad \text{expression (1)}$$

US 12,680,992 B2

31 where "Da" denotes a diameter of an unswaged section that is a section of the elastic body not swaged by the diameter-reduced portion, "Db" denotes a diameter of a swaged section that is a section of the elastic body swaged by the diameter-reduced portion, "Sa" denotes a surface area of a section of the covered section of the lead accommodated in the through-hole in the swaged section, "Fc" denotes a magnitude of a load in the axial direction that interrupts electrical connection between the element electrode and the terminal fitting, "μ" denotes a coefficient of static friction between the elastic body and the covered section of the lead, and "q" denotes pressure per unit area applied to the covered section of the lead by the elastic body when the diameter-reduced portion radially swages the elastic body by a unit length.

2. The gas sensor according to claim 1, further comprising:

a ceramic housing accommodating the element electrode and a front end section of the terminal fitting electrically connected to the element electrode; and a spacer disposed between the ceramic housing and the elastic body in the axial direction.

3. The gas sensor according to claim 2, wherein the lead retaining portion of the terminal fitting is disposed inside the spacer.

4. The gas sensor according to claim 1, wherein a material of the elastic body is fluoro-rubber.

5. The gas sensor according to claim 1, wherein the covered section of the lead is covered with fluoro-resin.

6. The gas sensor according to claim 1, wherein the diameter Da of the unswaged section and the diameter Db of the swaged section satisfy an expression (2) given below:

$$Db/Da \geq 0.5. \qquad \text{expression (2)}$$

7. The gas sensor according to claim 2, wherein a material of the clastic body is fluoro-rubber.

8. The gas sensor according to claim 2, wherein the covered section of the lead is covered with fluoro-resin.

9. The gas sensor according to claim 2, wherein the diameter Da of the unswaged section and the diameter Db of the swaged section satisfy an expression (2) given below:

$$Db/Da \geq 0.5. \qquad \text{expression (2)}$$

* * * * *